US009234211B2

(12) United States Patent
Kim et al.

(10) Patent No.: US 9,234,211 B2
(45) Date of Patent: Jan. 12, 2016

(54) HYBRID PROMOTER AND RECOMBINANT VECTOR COMPRISING THE SAME

(75) Inventors: Yeon Chul Kim, Daejeon (KR); Saem Jung, Daejeon (KR); Jun Jung, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 13/990,546

(22) PCT Filed: Nov. 29, 2011

(86) PCT No.: PCT/KR2011/009166
§ 371 (c)(1), (2), (4) Date: Aug. 16, 2013

(87) PCT Pub. No.: WO2012/074277
PCT Pub. Date: Jun. 7, 2012

(65) Prior Publication Data

US 2013/0324593 A1 Dec. 5, 2013

(30) Foreign Application Priority Data

Nov. 30, 2010 (KR) ........................ 10-2010-0120884

(51) Int. Cl.

| | |
|---|---|
| ***C07H 21/04*** | (2006.01) |
| ***C12N 15/85*** | (2006.01) |
| *C12N 5/07* | (2010.01) |
| *C12N 5/10* | (2006.01) |
| *C12N 5/071* | (2010.01) |
| *C12N 5/16* | (2006.01) |
| *C12N 15/00* | (2006.01) |
| *C12P 21/04* | (2006.01) |
| *C12P 21/06* | (2006.01) |

(52) U.S. Cl.
CPC ............ *C12N 15/85* (2013.01); *C12N 2830/15* (2013.01); *C12N 2830/36* (2013.01); *C12N 2830/42* (2013.01); *C12N 2830/60* (2013.01); *C12N 2830/80* (2013.01); *C12N 2830/85* (2013.01)

(58) Field of Classification Search
None
See application file for complete search history.

(56) References Cited

U.S. PATENT DOCUMENTS

| | | | | |
|---|---|---|---|---|
| 7,423,135 | B2 * | 9/2008 | Estes et al. | 536/23.1 |
| 7,626,075 | B2 * | 12/2009 | Beschorner et al. | 800/8 |
| 7,824,907 | B2 * | 11/2010 | Chatellard et al. | 435/320.1 |
| 8,298,816 | B2 | 10/2012 | Tsunoda et al. | |
| 2007/0161110 | A1 | 7/2007 | Iida et al. | |
| 2009/0156498 | A1 * | 6/2009 | Pardridge et al. | 514/12 |
| 2010/0216188 | A1 | 8/2010 | Hui | |

FOREIGN PATENT DOCUMENTS

| | | | |
|---|---|---|---|
| EP | 1 816 203 | A1 | 8/2007 |
| JP | H03-168087 | A | 7/1991 |
| JP | 2008-521384 | A | 6/2008 |
| JP | 2008-529518 | A | 8/2008 |
| JP | 2008-283882 | A | 11/2008 |
| JP | 2010-168288 | A | 8/2010 |
| KR | 10-0808269 | A | 2/2008 |
| WO | WO 2005/000888 | | 1/2005 |
| WO | WO 2005/054467 | A1 | 6/2005 |
| WO | WO 2005/071092 | A1 | 8/2005 |
| WO | WO 2006/095156 | A1 | 9/2006 |
| WO | WO 2009/105786 | A2 | 8/2009 |

OTHER PUBLICATIONS

Xu, Z-L., et al., "Optimization of transcriptional regulatory elements for constructing plasmid vectors," *Gene* 272:149-156, Elsevier Science B.V., Netherlands (2001).
Xu, Z-L., et al., "Strength evaluation of transcriptional regulatory elements for transgene expression by adenovirus vector," *Journal of Controlled Release 81*:155-163, Elssevier Science B.V., Netherlands (2002).
International Search Report and Written Opinion for International Application No. PCT/KR2011/009166, Korean Intellectual Property Office, Republic of Korea, mailed Jun. 20, 2012, 8 pages.
English language Abstract of Korean Patent Publication No. KR 10-2008-0007832 A, Korea Intellectual Property Rights Information Service—Korea (2008).
English language Abstract of Japanese Patent Publication No. JP 2008-283882 A, Industrial Property Digital Library—Japan (2008).
Lingfei, X., et at, "CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice," *Human Gene Therapy* 12:563-573, Mary Ann Liebert, Inc., United States (2001).
Supplementary European Search Report for European Patent Application EP 11 84 5541, Munich, Germany, completed Mar. 11, 2015.

* cited by examiner

*Primary Examiner* — Nancy J Leith
(74) *Attorney, Agent, or Firm* — Sterne, Kessler, Goldstein & Fox P.L.L.C.

(57) ABSTRACT

The present invention relates to a hybrid promoter, in which a whole or a part of a CMV enhancer, a whole or a part of a β-actin promoter, a whole or a part of a CMV promoter, and a whole or a part of a β-actin intron are operably linked to each other, a recombinant vector comprising the same, a transformant transformed with the recombinant vector, a pharmaceutical composition comprising the recombinant vector or the transformant, and a method for preparing a target protein using the recombinant vector or the transformant. The hybrid promoter of the present invention is able to induce high expression of a target protein in a eukaryotic cell. Therefore, the hybrid promoter of the present invention can be effectively used for the development of an antibody or the production of a DNA vaccine.

12 Claims, 9 Drawing Sheets

*Please note that there are two *BstX* I sites in the polylinker.

SEQUENCE LISTING

```
<160> NUMBER OF SEQ ID NOS: 14

<210> SEQ ID NO 1
<211> LENGTH: 29
<212> TYPE: DNA
<213> ORGANISM: Artificial Sequence
<220> FEATURE:
<223> OTHER INFORMATION: Forward primer for beta-actin promoter

<400> SEQUENCE: 1

cagctagcgg gaccaagaca gaaccataa                                        29


<210> SEQ ID NO 2
<211> LENGTH: 28
<212> TYPE: DNA
<213> ORGANISM: Artificial Sequence
<220> FEATURE:
<223> OTHER INFORMATION: Reverse primer for beta-actin promoter

<400> SEQUENCE: 2

gtaagcttcg gcgaactata tcagggca                                         28


<210> SEQ ID NO 3
<211> LENGTH: 30
<212> TYPE: DNA
<213> ORGANISM: Artificial Sequence
<220> FEATURE:
<223> OTHER INFORMATION: Forward primer for beta-actin promoter

<400> SEQUENCE: 3

cacgctagct ctctcttttt ttttttttat                                       30


<210> SEQ ID NO 4
<211> LENGTH: 27
<212> TYPE: DNA
<213> ORGANISM: Artificial Sequence
<220> FEATURE:
<223> OTHER INFORMATION: Forward primer for TATA box of CMV promoter

<400> SEQUENCE: 4

cagtcgacta ggcgtgtacg gtgggag                                          27


<210> SEQ ID NO 5
<211> LENGTH: 18
<212> TYPE: DNA
<213> ORGANISM: Artificial Sequence
<220> FEATURE:
<223> OTHER INFORMATION: Reverse primer for TATA box of CMV promoter

<400> SEQUENCE: 5

tagaaggcac agtcgagg                                                    18


<210> SEQ ID NO 6
<211> LENGTH: 35
<212> TYPE: DNA
<213> ORGANISM: Artificial Sequence
<220> FEATURE:
<223> OTHER INFORMATION: Forward primer for beta-actin intron
```

-continued

<400> SEQUENCE: 6
caagagctct ctggctaact gagcacaggc ctttc 35

<210> SEQ ID NO 7
<211> LENGTH: 27
<212> TYPE: DNA
<213> ORGANISM: Artificial Sequence
<220> FEATURE:
<223> OTHER INFORMATION: Forward primer for CMV enhancer

<400> SEQUENCE: 7
cagacgcgtt gacattgatt attgact 27

<210> SEQ ID NO 8
<211> LENGTH: 27
<212> TYPE: DNA
<213> ORGANISM: Artificial Sequence
<220> FEATURE:
<223> OTHER INFORMATION: Reverse primer for CMV enhancer

<400> SEQUENCE: 8
caggctagca gttgttacga cattttg 27

<210> SEQ ID NO 9
<211> LENGTH: 1930
<212> TYPE: DNA
<213> ORGANISM: Cricetulus griseus
<220> FEATURE:
<221> NAME/KEY: promoter
<222> LOCATION: (1)..(1930)
<223> OTHER INFORMATION: Beta-actin promoter

<400> SEQUENCE: 9
gctagcggga ccaagacaga accataagcc agtgggatag atcagaaatg ttccagaggt 60
gggatggggc cagagtgcct gccccttgaa ccgtcccagg gaccagaggt gacaaagtgg 120
caacacaggt cctgcctggg aatctggtct gctcctactt agtaaagctg cctggtgtca 180
cacaagaggc ccccacttat tcctgcaccc ctggtggtag gtggcgtctt ctcccctgca 240
gccaccaggc tcccctgaga acactgccgg cagtcctcat tgacaggcag tattcgctct 300
gccccacccc cacctgtgaa ttgcagggct ggcaggtcct caggcagctg gcaaaccgcc 360
tgaacaactg agagatacag ggccagggcc agggcagtcc cgtcccccgg aggcagggag 420
gggacgtgct gggaaagttc tctctctcag gcccaggttg gtgactgcag aaggcttctg 480
tcaaatctct tttgtgggaa ccacagagta gccctgaacg tgggggtgtg cttccagtat 540
actctggggt caccctttcc atactggagg cctctgcaac ttcaaaatgc tctgctacca 600
acctagcaca aggaagttgg tccagcctcc ccacgcaagg ccactgctgc agtccatata 660
tggactaagc cttccttggt ttcaacacct acactcactg agcccctact atgtgtatgc 720
agagccgaga caggccctga gcatctcatc tgaagcgccc ttcttgccta aattcagttt 780
tctgtcactt tctcccagga ggtgtgtgtc cctctaagct aagccagggg tccctcaccc 840
ctgccccact cccatcccta gtgtaggtat cagctgaaga gcttcctgag cagaacactc 900
ttgggtgctg acattttgat aaataggccc atgttgagga gagcaggggt ccgggggcgg 960
gagatcttct ctggtggatt gagggctcca agaactactc tttgagcacg ctgtccctcc 1020
cagagtcccc acagcctcca gatggactag aacacagttc ggctgtggct gcacataact 1080
aacagaggat agatggtggg tcccagccca acagtgcctg gcaatcaccc agagccacca 1140
gctaacggcc ttggcttagt tttttgcctg ggtgtgatca ggcagccctc caaaactgcc 1200

-continued

```
cggactccat gacaagtttt gcttgttcta tagagcacag ttcctttcta ggtctggggc   1260

gagggacatc gggagacatc ttcctgcaac agctccagtc actggaccac caggctcgcc   1320

ctgtctttgg tgtgtggccc tgagtctcct aagtggccca aacctgtgaa gacccctcca   1380

accacagttt tgcttctaaa ttgtacccca acacacctag caaattgaaa ccccaccaga   1440

agtcccccag atctggcttt ccggctattg ctggcaaggg ggagtgactc ccggcccatt   1500

caatccaggc cccgcgtgtt cctcaaacaa gaagccacgt aaacataaac cgagcctcca   1560

tgctgaccct tgcccatcga ggtactcaat gttcacgtga tatccacacc cagagggtcc   1620

tggggtgggt gcatgagccc cagaatgcag gcttgataac cgagaccctg aatcgggcag   1680

tgtccacaag ggcggaggcc agtcatgcat gttcgggcct atggggccag cacccaacgc   1740

caaaactctc catcctcttc ctcaatctcg ctttctctct ctctctcttt tttttttttt   1800

tttttttttt ttttgcaaaa ggaggggaga gggggtaaaa aaatgctgca ctgtgcggct   1860

aggccggtga gtgagcggcg cggagccaat cagcgctcgc cgttccgaaa gttgcctttt   1920

atggctcgac                                                          1930
```

```
<210> SEQ ID NO 10
<211> LENGTH: 154
<212> TYPE: DNA
<213> ORGANISM: Cricetulus griseus
<220> FEATURE:
<221> NAME/KEY: promoter
<222> LOCATION: (1)..(154)
<223> OTHER INFORMATION: U20114 Beta-actin promoter

<400> SEQUENCE: 10

gctagctctc tctttttttt tttttatttt ttttttttgc aaaaggaggg gagagggggt     60

aaaaaaatgc tgcactgtgc ggctaggccg gtgagtgagc ggcgcggagc caatcagcgc    120

tcgccgttcc gaaagttgcc ttttatggct cgac                                154
```

```
<210> SEQ ID NO 11
<211> LENGTH: 130
<212> TYPE: DNA
<213> ORGANISM: Human herpesvirus
<220> FEATURE:
<221> NAME/KEY: promoter
<222> LOCATION: (1)..(130)
<223> OTHER INFORMATION: CMV promoter TATA box

<400> SEQUENCE: 11

taggcgtgta cggtgggagg tctatataag cagagctctc tggctaacta gagaacccac     60

tgcttactgg cttatcgaaa ttaatacgac tcactatagg gagacccaag ctggctagcg    120

tttaaactta                                                           130
```

```
<210> SEQ ID NO 12
<211> LENGTH: 1019
<212> TYPE: DNA
<213> ORGANISM: Cricetulus griseus
<220> FEATURE:
<221> NAME/KEY: Intron
<222> LOCATION: (1)..(1019)
<223> OTHER INFORMATION: Beta-actin intron

<400> SEQUENCE: 12

ctagcgagca caggcctttc gcagctcttt cttcgccgct ccacacccgc caccaggtaa     60

gcagggacaa caggcccagc cggccacagc cctcccgtgg gcagtgaccg cgctgcaggg    120

tcgcggggga cactcggcgc ggacaccggg gaaggctgga gggtggtgcc gggccgcgga    180
```

-continued

```
gcggacactt tcagatccaa ctttcagtcc agggtgtaga ccctttacag ccgcattgcc    240

acggtgtaga caccggtgga cccgctctgg ctcagagcac gcggcttggg ggaacccatt    300

agggtcgcag tgtgggcgct atgagagccg atgcagcttt cgggtgttga accgtatctg    360

cccaccttgg ggggaggaca caaggtcggg agccaaacgc cacgatcatg ccttggtggc    420

ccatgggtct ttgtctaaac cggtttgccc atttggcttg ccgggcgggc gggcgcggcg    480

ggcccggctc ggccgggtgg gggctgggtt gccactgcgc ttgcgcgctc tatggctggg    540

tattggggcg cgtgcacgct ggggagggag cccttcctct tccccctctc ccaagttaaa    600

cttgcgcgtg cgtattgaga cttggagcgc ggccaccggg gttgggcgag ggcggggccg    660

ttgtccggaa ggggcggggt cgcagcggct tcggggcgcc tgctcgcgct tcctgctggg    720

tgtggtcgcc tcccgcgcgc gcactagccg cccgccggcg ggcgaaggc ggggcttgcg    780

cccgtttggg gagggggcgg aggcctggct tcctgccgtg gggccgcctc cggaccagcg    840

tttgcctctt atggtaataa cgcggccggc ctgggcttcc tttgtcccct gagtttgggc    900

gcgcgccccc tggcggcccg aggccgcggc ttgccggaag tgggcagggc ggcagcggct    960

gcgcctagtg gcccgctagt gaccgcgacc ctcttttgtg ccctgatata gttcgccga    1019


<210> SEQ ID NO 13
<211> LENGTH: 530
<212> TYPE: DNA
<213> ORGANISM: Human herpesvirus
<220> FEATURE:
<221> NAME/KEY: enhancer
<222> LOCATION: (1)..(530)
<223> OTHER INFORMATION: CMV enhancer

<400> SEQUENCE: 13

acgcgttgac attgattatt gactagttat taatagtaat caattacggg gtcattagtt     60

catagcccat atatggagtt ccgcgttaca taacttacgg taaatggccc gcctggctga    120

ccgcccaacg acccccgccc attgacgtca ataatgacgt atgttcccat agtaacgcca    180

atagggactt tccattgacg tcaatgggtg gactatttac ggtaaactgc ccacttggca    240

gtacatcaag tgtatcatat gccaagtacg ccccctattg acgtcaatga cggtaaatgg    300

cccgcctggc attatgccca gtacatgacc ttatgggact ttcctacttg gcagtacatc    360

tacgtattag tcatcgctat taccatggtg atgcggtttt ggcagtacat caatgggcgt    420

ggatagcggt ttgactcacg gggatttcca agtctccacc ccattgacgt caatgggagt    480

ttgttttggc accaaaatca acgggacttt ccaaaatgtc gtaacaactg              530


<210> SEQ ID NO 14
<211> LENGTH: 450
<212> TYPE: DNA
<213> ORGANISM: Artificial Sequence
<220> FEATURE:
<223> OTHER INFORMATION: TATA box region of a CMV promoter of a pcDNA3.1
      vector

<400> SEQUENCE: 14

cattgacgtc aatgggagtt tgttttggca ccaaaatcaa cgggactttc caaaatgtcg     60

taacaactcc gccccattga cgcaaatggg cggtaggcgt gtacggtggg aggtctatat    120

aagcagagct ctctggctaa ctagagaacc cactgcttac tggcttatcg aaattaatac    180

gactcactat agggagaccc aagctggcta gcgtttaaac ttaagcttgg taccgagctc    240

ggatccacta gtccagtgtg gtggaattct gcagatatcc agcacagtgg cggccgctcg    300
```

-continued

| | |
|---|---|
| agtctagagg gcccgtttaa acccgctgat cagcctcgac tgtgccttct agttgccagc | 360 |
| catctgttgt ttgcccctcc cccgtgcctt ccttgaccct ggaaggtgcc actcccactg | 420 |
| tcctttccta ataaaatgag gaaattgcat | 450 |

HYBRID PROMOTER AND RECOMBINANT VECTOR COMPRISING THE SAME

REFERENCE TO RELATED APPLICATIONS

Related International Application No. PCT/KR2011/009166, filed Nov. 29, 2011, and Korean Patent Application No. 10-2010-0120884, filed Nov. 30, 2010, are herein incorporated by reference in their entireties.

REFERENCE TO SEQUENCE LISTING SUBMITTED ELECTRONICALLY VIA EFS-WEB

The content of the electronically submitted sequence listing (Name: 2972_0020001 SEQIDListingascii_v2.txt; Size: 8,664 bytes; and Date of Creation: May 13, 2015) is incorporated by reference in its entirety.

TECHNICAL FIELD

The present invention relates to a hybrid promoter, in which a whole or a part of a CMV enhancer, a whole or a part of a β-actin promoter, a whole or a part of a CMV promoter, and a whole or a part of a β-actin intron are operably linked to each other, a recombinant vector comprising the same, a transformant transformed with the recombinant vector, a pharmaceutical composition comprising the recombinant vector or the transformant, and a method for preparing a target protein using the recombinant vector or the transformant.

BACKGROUND ART

In order to express a target gene in a host cell, an expression vector and a gene transfer technique for carrying a structural gene of interest and expressing the same within the cells are required. In this regard, the expression vector capable of expressing a DNA fragment inserted therein generally includes regulatory elements, such as a promoter or an enhancer. Such regulatory elements facilitate the expression of a target gene operably linked thereto. The expression vectors can be selected depending on host cell type, target gene expression level, type of expression desired and the like, and a variety of expression vectors have been developed to satisfy the desired purposes.

DISCLOSURE OF INVENTION

Technical Problem

Accordingly, the present inventors have made an effort to develop an expression vector suitable for increasing an expression level of a target protein, and found that a hybrid promoter, in which a whole or a part of a CMV enhancer, a whole or a part of a β-actin promoter, a whole or a part of a CMV promoter, and a whole or a part of a β-actin intron are operably linked, is able to remarkably increase the expression level of the target protein, thereby completing the present invention.

Solution to Problem

An object of the present invention is to provide a hybrid promoter, in which a whole or a part of a CMV enhancer, a whole or a part of a β-actin promoter, a whole or a part of a CMV promoter, and a whole or a part of a β-actin intron are operably linked to each other.

Another object of the present invention is to provide a recombinant vector, comprising the hybrid promoter and a target protein-encoding gene operably linked thereto.

Still another object of the present invention is to provide a transformant into which the recombinant vector is introduced.

Still another object of the present invention is to provide a pharmaceutical composition comprising the recombinant vector or the transformant.

Still another object of the present invention is to provide a method for preparing a target protein, comprising the steps of:

1) culturing the transformant of the present invention;

2) inducing the expression of a target protein from the transformant; and 3) harvesting the expressed target protein from the transformant or the culture solution thereof.

Advantageous Effects of Invention

The present invention relates a novel hybrid promoter that is optimized for the production of an antibody or a DNA vaccine. When a variety of target genes are inserted into a recombinant vector including the hybrid promoter, transcription and expression of the target genes can be improved. Therefore, the recombinant vector including the hybrid promoter of the present invention can be effectively used for the development of an antibody or the production of a DNA vaccine.

BEST MODE FOR CARRYING OUT THE INVENTION

Figure 1:
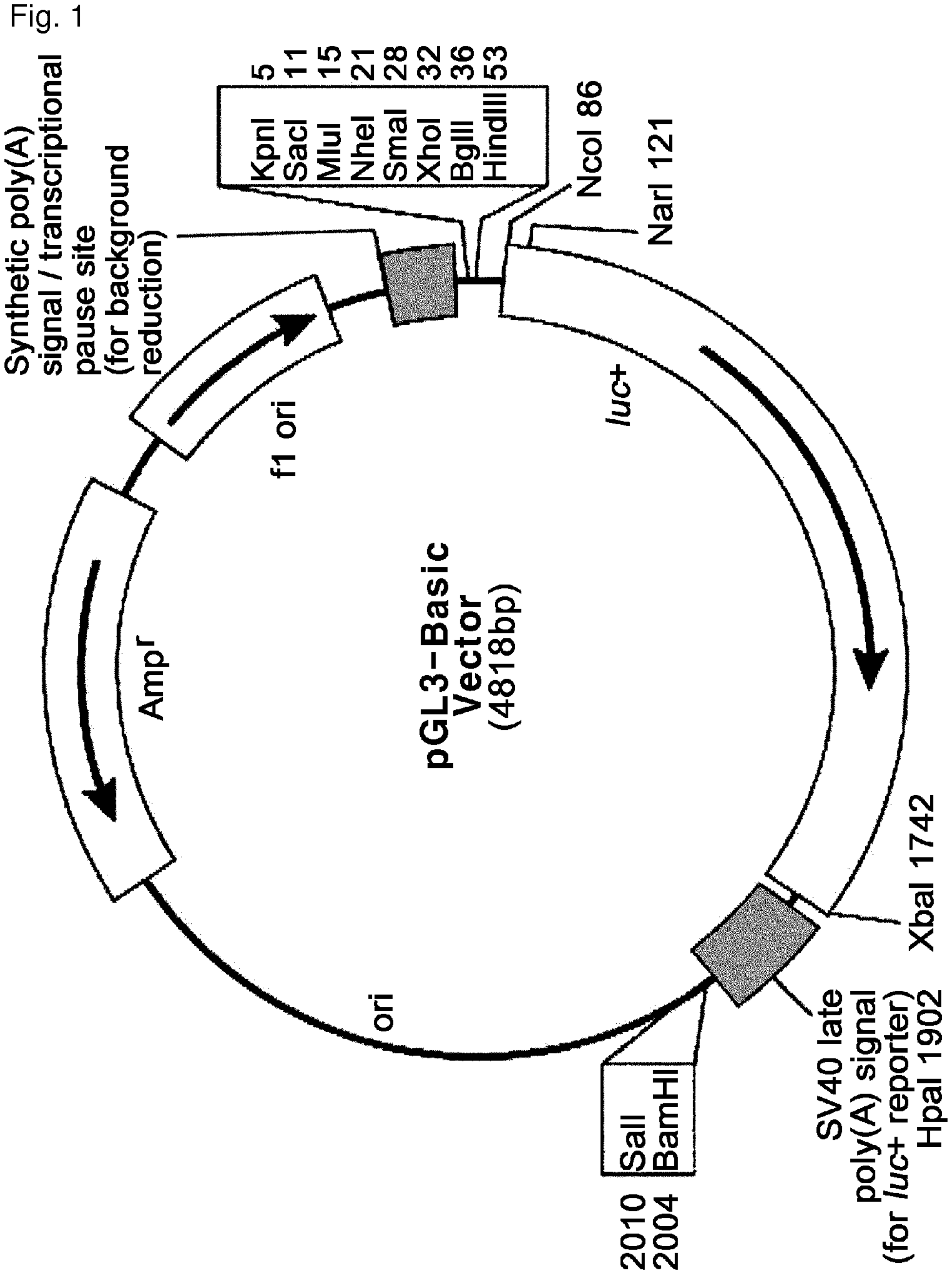
FIG. 1 shows the structure of a pGL3-Basic vector, which is used as a starting vector in the present invention.

In one embodiment, the present invention provides a hybrid promoter, in which a whole or a part of a CMV enhancer, a whole or a part of a β-actin promoter, a whole or a part of a CMV promoter, and a whole or a part of a β-actin intron are operably linked to each other.

As used herein, the term "β-actin" exists in most cell types as a major component of the cytoskeleton and is a highly conserved protein that is involved in cell motility, structure and integrity. The gene encoding β-actin serves as a housekeeping gene, and can maintain a certain level of expression regardless of environmental conditions.

As used herein, the term "promoter" refers to a polynucleotide sequence that allows transcription of a target gene operably linked thereto and regulates expression thereof. The promoter includes sequences that are recognized by a RNA polymerase and a transcription initiation site. In order to express a target protein in a particular cell type or a host cell, a suitable functional promoter must be chosen carefully. For example, the promoter sequences have been deposited in data banks such as GenBank, and may be obtained as a separate element or elements cloned within a polynucleotide sequence from commercial or individual sources.

As used herein, the term "β-actin promoter" refers to a structural gene that is involved in the regulation of transcriptional activity of the housekeeping gene, β-actin. In case of influencing on the expression of a coding sequence under transcriptional regulation of a promoter, the β-actin promoter is operably linked to a coding sequence. The coding sequence may be operably linked to a nucleotide sequence regulating the transcription in a forward or reverse direction.

With respect to the objects of the present invention, the β-actin promoter of the present invention can be composed of one or more DNA fragments selected from the group consisting of the following:

i) a DNA fragment having a nucleotide sequence represented by SEQ ID NO: 9, ii) a DNA fragment having a nucleotide sequence represented by SEQ ID NO: 10, or iii) a DNA fragment having a deletion, a substitution or an insertion of one or more nucleotides in the nucleotide sequences of the DNA fragments i) and ii), and having a promoter activity and an activity of regulating the expression of a target gene operably linked downstream of the promoter.

The present invention may include DNA fragments whose nucleotide sequences have at least 80%, 90%, 95%, 96%, 97%, 98%, or 99% homology to those of the DNA fragments described above.

The β-actin promoter of the present invention can be amplified by PCR using forward and reverse primers represented by SEQ ID NOs: 1 and 2 and a whole or a part of the β-actin promoter sequence as a template. The resulting β-actin promoter can be a DNA fragment having a size of approximately 1.9 kb or 150 bp.

```
5'-BA 1_F(NheI):
                                        (SEQ ID NO: 1)
5'-CAG CTA GCG GGA CCA AGA CAG AAC CAT AA-3

3'-BA 4_R(HindIII):
                                        (SEQ ID NO: 2)
5'-GTA AGC TTC GGC GAA CTA TAT CAG GGC A-3
```

Any type of the β-actin promoters known in the art can be used as a β-actin promoter of the present invention without limitation, and the preferred β-actin promoter can be a β-actin promoter of CHO (Chinese Hamster Ovary) cell.

The DNA fragment of SEQ ID NO: 9 comprises nucleotide sequences of 1930 bp, which code for the full-length of a β-actin promoter derived from CHO cells, and the DNA fragment of SEQ ID NO: 10 comprises nucleotide sequences of 154 bp, which code for a U20114 fragment having a β-actin promoter activity.

As used herein, the term "β-actin intron" refers to a sequence regulating the transcription of a gene that is present inside the β-actin gene or a transcript thereof and that is not included in a final RNA product of the gene. The nucleotide sequence of an intron does not have information about an amino acid sequence.

With respect to the objects of the present invention, the β-actin intron of the present invention can be composed of a DNA fragment of the following:

i) a DNA fragment having a nucleotide sequence represented by SEQ ID NO: 12, or ii) a DNA fragment having a deletion, a substitution or an insertion of one or more nucleotides in the nucleotide sequence of the DNA fragment i), and having a promoter activity and an activity of regulating the expression of a target gene operably linked downstream of the promoter.

The present invention may include DNA fragments, whose DNA sequences have at least 80%, 90%, 95%, 96%, 97%, 98%, or 99% homology to those of the DNA fragments described above.

The β-actin intron of the present invention can be amplified by PCR using forward and reverse primers represented by SEQ ID NOs: 6 and 2 and a whole or a part of the β-actin intron sequence as a template. The resulting β-actin intron can be a DNA fragment having a size of approximately 1 kb.

```
5'-CBint_F(NheI):
                                        (SEQ ID NO: 6)
5'-CAA GCT AGC GAG CAC AGG CCT TTC-3'

3'-BA 4_R(HindIII):
                                        (SEQ ID NO: 2)
5'-GTA AGC TTC GGC GAA CTA TAT CAG GGC A-3'
```

As used herein, the term "CMV (cytomegalovirus)" belongs to a viral genus of the viral group known as *Herpesviridae*. The species that infects humans is commonly known as human CMV (HCMV) or human herpesvirus-5 (HHV-5). It is classified into the alpha-herpesvirus family, and gamma-herpesvirus family, and all herpesviruses share a characteristic ability to remain latent within the body over long periods.

As used herein, the term "CMV promoter (pCMV)" refers to a cytomegalovirus (CMV) early promoter. pCMV has been known as a powerful regulatory element, and shows its activity in various cells.

As used herein, the term "TATA box" refers to a region consisting of the nucleotide sequence of TATAAA, which is included in many eukaryotic promoters. The TATA box is typically located very close to a transcription initiation site (within 50 base pairs), and a TATA binding protein binds to this region to assist the formation of a RNA polymerase transcriptional complex.

With respect to the objects of the present invention, the TATA box region of the CMV promoter according to the present invention can be composed of a DNA fragment of the following:

i) a DNA fragment having a nucleotide sequence represented by SEQ ID NO: 11, or ii) a DNA fragment having a deletion, a substitution or an insertion of one or more nucleotides in the nucleotide sequence of the DNA fragment i), and having a promoter activity and an activity of regulating the expression of a target gene operably linked downstream of the promoter.

The present invention may include DNA fragments whose DNA sequences have at least 80%, 90%, 95%, 96%, 97%, 98%, or 99% homology to those of the DNA fragments described above.

As used herein, the term "TATA box" refers to a sequence of alternating thymine (T) and adenine (A) of a transcription initiation site present in the promoter region, and is a highly conserved region common in most organisms.

The TATA box region of the CMV promoter can be amplified by PCR using forward and reverse primers represented by SEQ ID NOs: 4 and 5 and a whole or a part of the TATA box region of the CMV promoter as a template. The resulting TATA box region can be a DNA fragment having a size of approximately 130 bp.

```
5'-CMV TA_F(SalI):
                                        (SEQ ID NO: 4)
5'-CAG TCG ACT AGG CGT GTA CGG TGG GAG-3'

3'-BGH reverse priming site:
                                        (SEQ ID NO: 5)
5'-TAG AAG GCA CAG TCG AGG-3'
```

As used herein, the term "CMV enhancer" refers to a sequence that binds to other protein of a transcription initiation complex and enhances the transcription initiation regulated by the related promoter.

With respect to the objects of the present invention, the CMV enhancer of the present invention can be composed of a DNA fragment of the following:

i) a DNA fragment having a nucleotide sequence represented by SEQ ID NO: 13, or ii) a DNA fragment having a deletion, a substitution or an insertion of one or more nucleotides in the nucleotide sequence of the DNA fragment i), and having a promoter activity and an activity of regulating the expression of a target gene operably linked downstream of the promoter.

The present invention may include DNA fragments whose DNA sequences have at least 80%, 90%, 95%, 96%, 97%, 98%, or 99% homology to those of the DNA fragments described above.

The CMV enhancer of the present invention can be amplified by PCR using forward and reverse primers represented by SEQ ID NOs: 7 and 8 and a whole or a part of the CMV enhancer as a template. The resulting CMV enhancer can be a DNA fragment having a size of approximately 530 bp.

```
5'-CMV En_F(MluI):
                                        (SEQ ID NO: 7)
5'-CAG ACG CGT TGA CAT TGA TTA TTG ACT-3'

3'-CMV En_R(NheI):
                                        (SEQ ID NO: 8)
5'-CAG GCT AGC AGT TGT TAC GAC ATT TTG-3'
```

As used herein, the term "PCR (Polymerase Chain Reaction)" means a scientific technique in molecular biology to amplify a single or a few copies of a piece of DNA across several orders of magnitude, generating thousands to millions of copies of a particular DNA sequence. The method relies on thermal cycling consisting of repeated cycles as follows:

1) denaturation step: heating a DNA template, yielding single-stranded DNA molecules, 2) annealing step: annealing primers to the single-stranded DNA template, and binding DNA polymerase to the primer-template hybrid, and 3) extension/elongation step: synthesizing a new DNA strand complementary to the DNA template strand, leading to exponential (geometric) amplification of the target DNA.

PCR provides a means to detect the presence of a target molecule under quantitative or semi-quantitative conditions and to determine the relative amount thereof within the starting pool of nucleic acids.

As used herein, the term "downstream" refers to a nucleotide sequence that is located 3' to a reference nucleotide sequence. In particular, downstream nucleotide sequences generally relate to sequences followed by a transcription initiation site. For example, a translation initiation codon of a gene is located downstream of the transcription initiation site.

As used herein, the term "operably linked" refers to a functional linkage between a promoter and a second sequence, wherein the promoter sequence initiates and mediates transcription of the DNA corresponding to the second sequence. In particular, the term operably linked means that the expression (operation) of a target gene sequence is located under the control of a transcription regulation sequence (e.g. promoter, enhancer or the like) or a translation regulation sequence.

Figure 9:
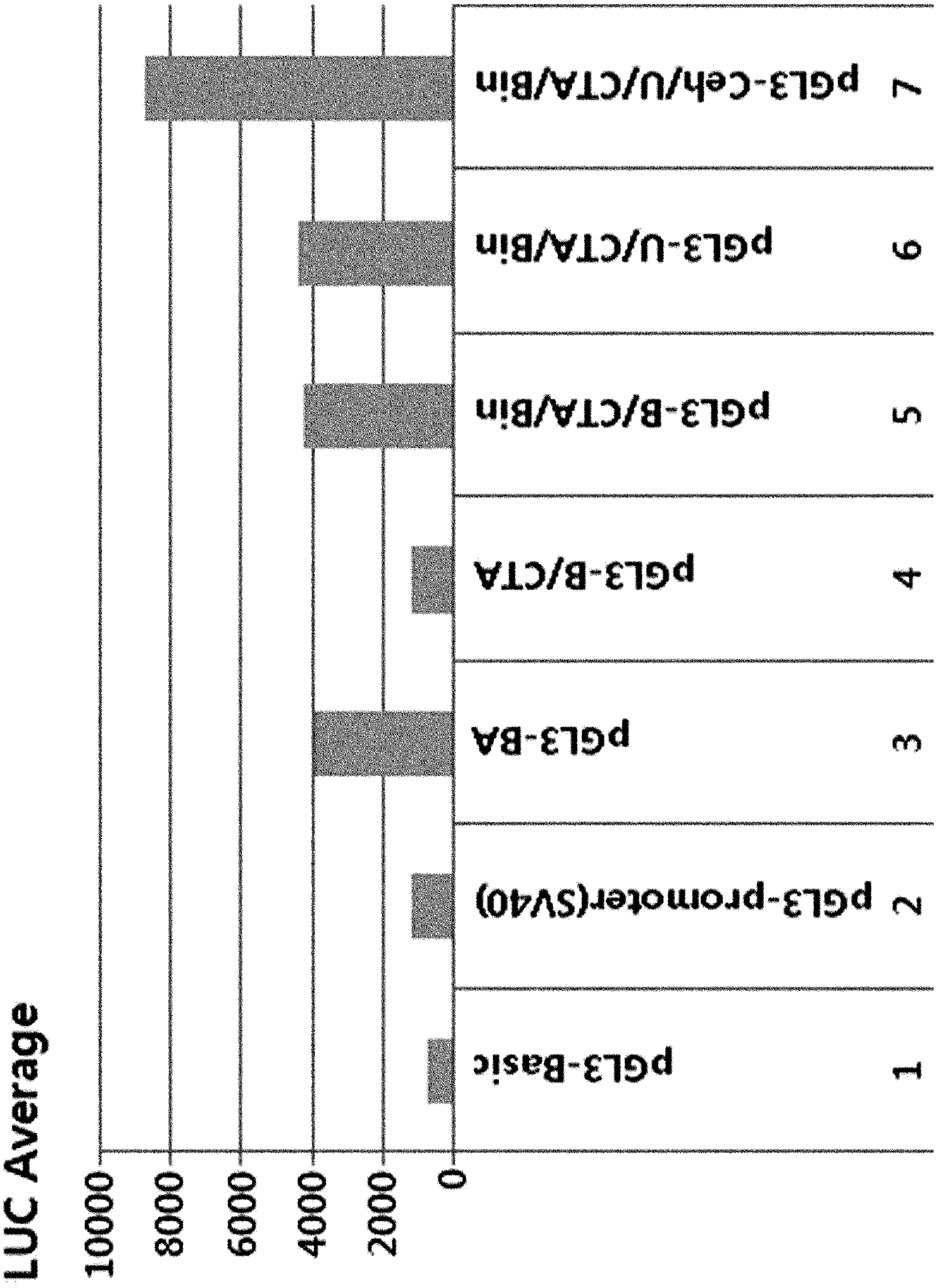
FIG. 9 shows the results of comparing luciferase expression levels in CHO cells transformed with each of the vectors described above.

In a preferred embodiment of the present invention, a hybrid promoter has been constructed, in which a whole or a part of a CMV enhancer, a whole or a part of a β-actin promoter, a whole or a part of a CMV promoter, and a whole or a part of a β-actin intron are operably linked to each other. It has been found that the hybrid promoter of the present invention can significantly improve the transcription of a target gene and the expression of a target protein, compared to conventional promoters known in the art (see FIG. 9).

In a more specific embodiment, the hybrid promoter of the present invention can be a promoter comprising:

a CMV enhancer represented by SEQ ID NO: 13, a TATA box region of a CMV promoter represented by SEQ ID NO: 11, a β-actin promoter represented by SEQ ID NO: 9, and a β-actin intron region represented by SEQ ID NO: 12, wherein the CMV promoter, TATA box, β-actin promoter and β-actin intron are operably linked to each other.

Further, the hybrid promoter of the present invention can be a promoter comprising:

a CMV enhancer represented by SEQ ID NO: 13, a TATA box region of a CMV promoter represented by SEQ ID NO: 11, a β-actin promoter represented by SEQ ID NO: 10, and a β-actin intron region represented by SEQ ID NO: 12, wherein the CMV promoter, TATA box, β-actin promoter and β-actin intron are operably linked to each other.

The hybrid promoter of the present invention may include substitution, insertion and deletion variants of one or more nucleotides, and combinations thereof. The substitution variant as used herein may be a variant, in which at least one base is removed and replaced with other base in the nucleotide sequence. The insertion variant as used herein may be a variant, in which one or more bases are introduced into a predetermined region within the nucleotide sequence. The deletion variant as used herein may be a variant, in which one or more bases are removed from the nucleotide sequence. In this regard, any combination of the substitution, deletion and insertion may be made to remain function of the components intact.

The hybrid promoter of the present invention may include DNA fragments, of which DNA sequences have at least 60%, 70%, 80%, 90%, 95%, 96%, 97%, 98% or 99% homology to those of the DNA fragment represented by SEQ ID NO: 13, the DNA fragment represented by SEQ ID NO: 11, the DNA fragment represented by SEQ ID NO: 9 or 10, and the DNA fragment represented by SEQ ID NO: 12.

As used herein, the term "homology" in relation to a sequence (e.g., a nucleic acid sequence, an amino acid sequence, etc.) refers to the proportion of identity between two or more gene sequences. Therefore, the greater the homology between two given genes, the greater the identity or similarity between their sequences. Whether or not two genes have homology is determined by comparing their sequences directly or by a hybridization method under stringent conditions. When two gene sequences are directly compared with each other, these genes have homology if the DNA sequences of the genes have representatively at least 50% identity, preferably at least 70% identity, more preferably at least 80%, 90%, 95%, 96%, 97%, 98%, or 99% identity with each other.

As used herein, the term "homologous" in all its grammatical forms and spelling variations refers to the relationship between proteins that possess a "common evolutionary origin," including superfamily-derived proteins (e.g., immunoglobulin superfamily) and homologous proteins derived from different species (e.g., myosin light chain) (Reeck et al., Cell 50: 667, 1987). Such proteins (and their encoding genes) have sequence homology, as reflected by their high degree of sequence similarity. However, in common usage and in the context of the present invention, the term "homologous" being modified with an adverb such as "highly" can refer to sequence similarity and not a common evolutionary origin.

As used herein, the term "sequence similarity" refers to the degree of identity or correspondence between nucleic acid or amino acid sequences of proteins that may or may not share a common evolutionary origin. In a specific embodiment, two DNA sequences are "substantially homologous" or "substantially similar" when at least approximately 21% (preferably at least approximately 50%, and most preferably, approximately 75%, 90%, 95%, 96%, 97%, 98% or 99%) of the nucleotides match over the defined length of the DNA sequences.

As used herein, the term "substantially similar" refers to nucleic acid fragments wherein changes in one or more nucleotide bases result in substitution of one or more amino acids, but do not affect the functional properties of the protein encoded thereby. "Substantially similar" also refers to nucleic acid fragments wherein changes in one or more nucleotide bases mediate alteration of gene expression by antisense or cosuppression technology without influencing the functional properties thereof. "Substantially similar" also refers to modifications of the nucleic acid fragments such as deletion or insertion of one or more nucleotide bases that do not substantially affect the functional properties of the resulting transcript. It is therefore understood that the present invention encompasses more than the specific exemplary sequences. Each of the proposed modifications is well known to those skilled in the art, as is the determination of retention of biological activities of the encoded products.

The similarity, identity and homology of amino acid sequences and base sequences are herein compared using FASTA with the default parameters. Alternatively, an identity search may be conducted, for example, using NCBI's BLAST 2.2.9 (published May 12, 2004). As used herein, the value of identity usually refers to the value as a result of alignment with the BLAST as described above using the default parameters. If the change of parameters results in higher values, then the highest value is employed herein as the value of the identity. When a plurality of regions is evaluated for identity, the highest value is employed herein as the value of the identity.

In another embodiment, the present invention provides a recombinant vector comprising the hybrid promoter and a target protein-encoding gene operably linked thereto.

As used herein, the term "recombinant vector" refers to a vector transferring a polynucleotide sequence of interest to a target cell. Such a vector is capable of self-replication or incorporation into a chromosome in a host cell (e.g., a prokaryotic cell, yeast, an animal cell, a plant cell, an insect cell, an individual animal, and an individual plant, etc.), and contains a promoter at a site suitable for transcription of a polynucleotide of the present invention. The recombinant vector may comprise a structural gene and a promoter for regulating expression thereof, and in addition, various regulatory elements in a state that allows them to operate within host cells. It is well known in the art that a type of recombinant vector of a living organism such as an animal and a species of a regulatory element used may vary depending on the type of host cell used.

In a specific embodiment, the recombinant vector of the present invention may include the hybrid promoter. More specifically, the present invention provides a recombinant vector comprising the hybrid promoter, in which a whole or a part of a CMV enhancer, a whole or a part of a β-actin promoter, a whole or a part of a CMV promoter, and a whole or a part of a β-actin intron are operably linked to each other.

Figure 8:
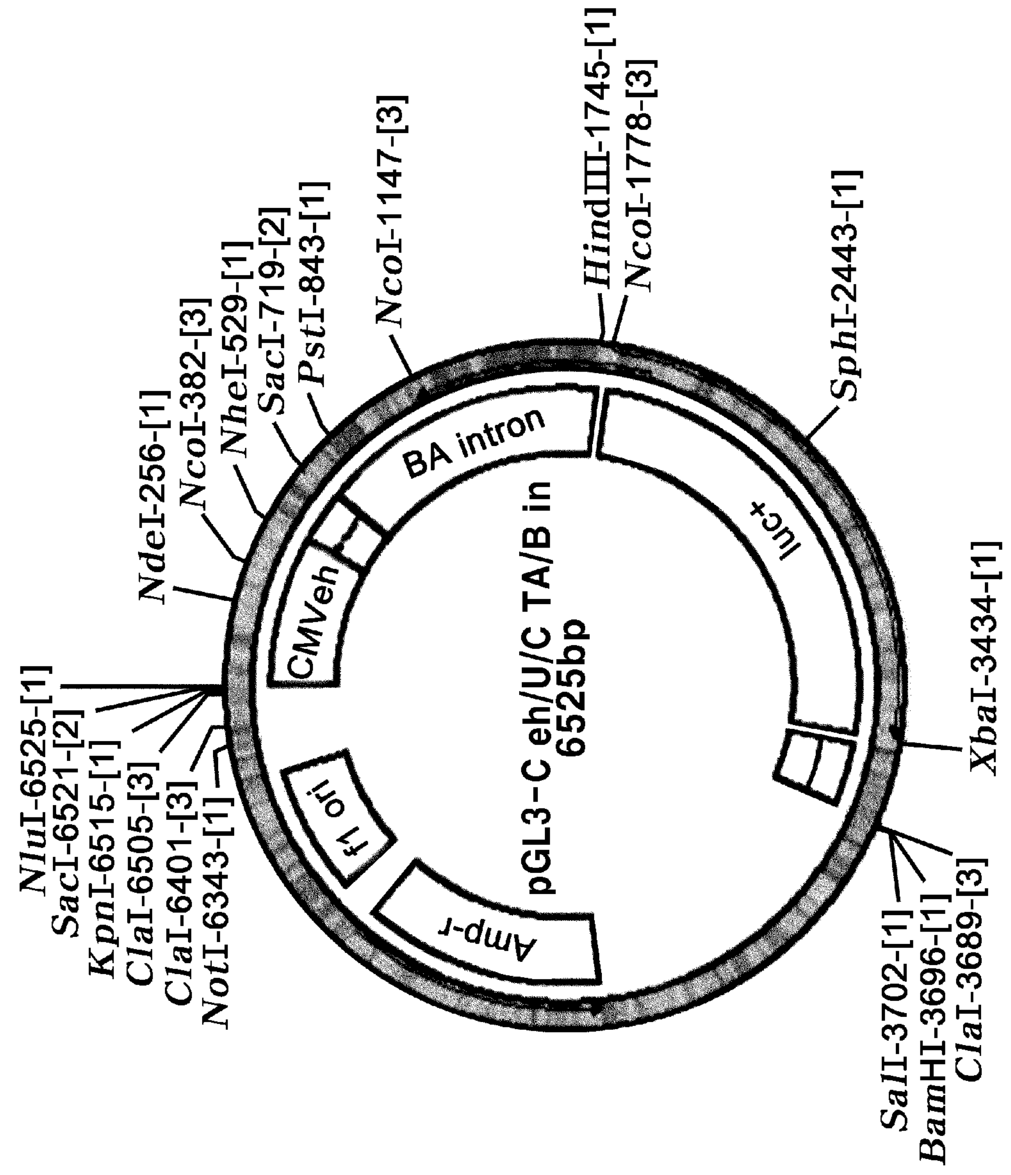
FIG. 8 shows the structure of a pGL3-$C_{eh}$/U/$C_{TA}$/$B_{in}$ vector, in which a hybrid promoter comprising a β-actin promoter (150 bp), a TATA box region of a CMV promoter (130 bp), a β-actin intron region and a CMV enhancer region is introduced into a pGL3-Basic vector.

More preferably, the recombinant vector of the present invention may include the hybrid promoter, in which a CMV enhancer represented by SEQ ID NO: 13, a TATA box region of a CMV promoter represented by SEQ ID NO: 11, a β-actin promoter represented by SEQ ID NO: 9 or 10, and a β-actin intron region represented by SEQ ID NO: 12 are operably linked to each other. Most preferably, the recombinant vector of the present invention may be a pGL3-$C_{eh}$/U/$C_{TA}$/$B_{in}$ vector having a cleavage map as shown in FIG. 8. It has been found that the recombinant vector of the present invention can induce the transcription of a target gene and the expression of a target protein with excellent efficiency (see FIG. 9).

The recombinant vector of the present invention may further include one or more regulatory elements such as a replication origin, selectable markers, terminators and the like.

As used herein, the term "selectable marker" refers to a gene which functions as guidance for selecting a host cell comprising a nucleic acid construct or a vector. The selectable markers may include, but are not limited to: fluorescent markers, luminescent markers and drug selectable markers, and the like. The fluorescent markers may include, but are not limited to, genes encoding fluorescence proteins such as green fluorescent protein (GFP), cyan fluorescent protein (CFP), yellow fluorescent protein (YFP), red fluorescent protein (dsRFP) and the like. The luminescent markers may include, but are not limited to, genes encoding luminescent proteins such as luciferases. The drug selectable markers suitable in the present invention may include, but are not limited to, resistance genes to antibiotics, such as ampicillin, streptomycin, gentamicin, kanamycin, hygromycin, tetracycline, chloramphenicol, and neomycin.

As used herein, the term "terminator" refers to a sequence which is located downstream of a protein-encoding region of a gene and which is involved in the termination of transcription when DNA is transcribed into mRNA, and the addition of a poly-A sequence. It is known that a terminator contributes to the stability of mRNA, and has an influence on the amount of gene expression. Terminators include, but are not limited to, a sequence including AATAAA.

Figure 2:
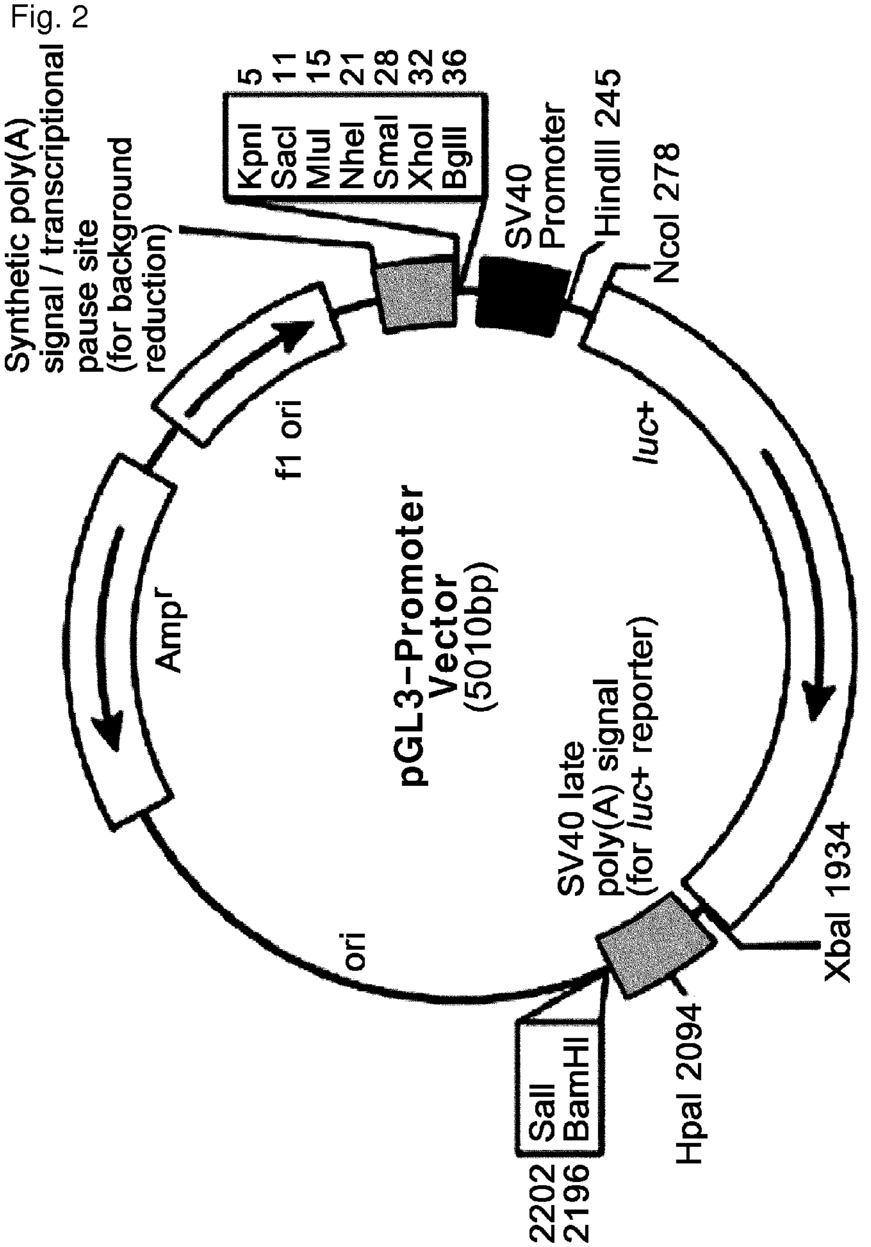
FIG. 2 shows the structure of a pGL3-Promoter (SV40) vector, in which a SV40 promoter is introduced into a pGL3-Basic vector.
Figure 3:
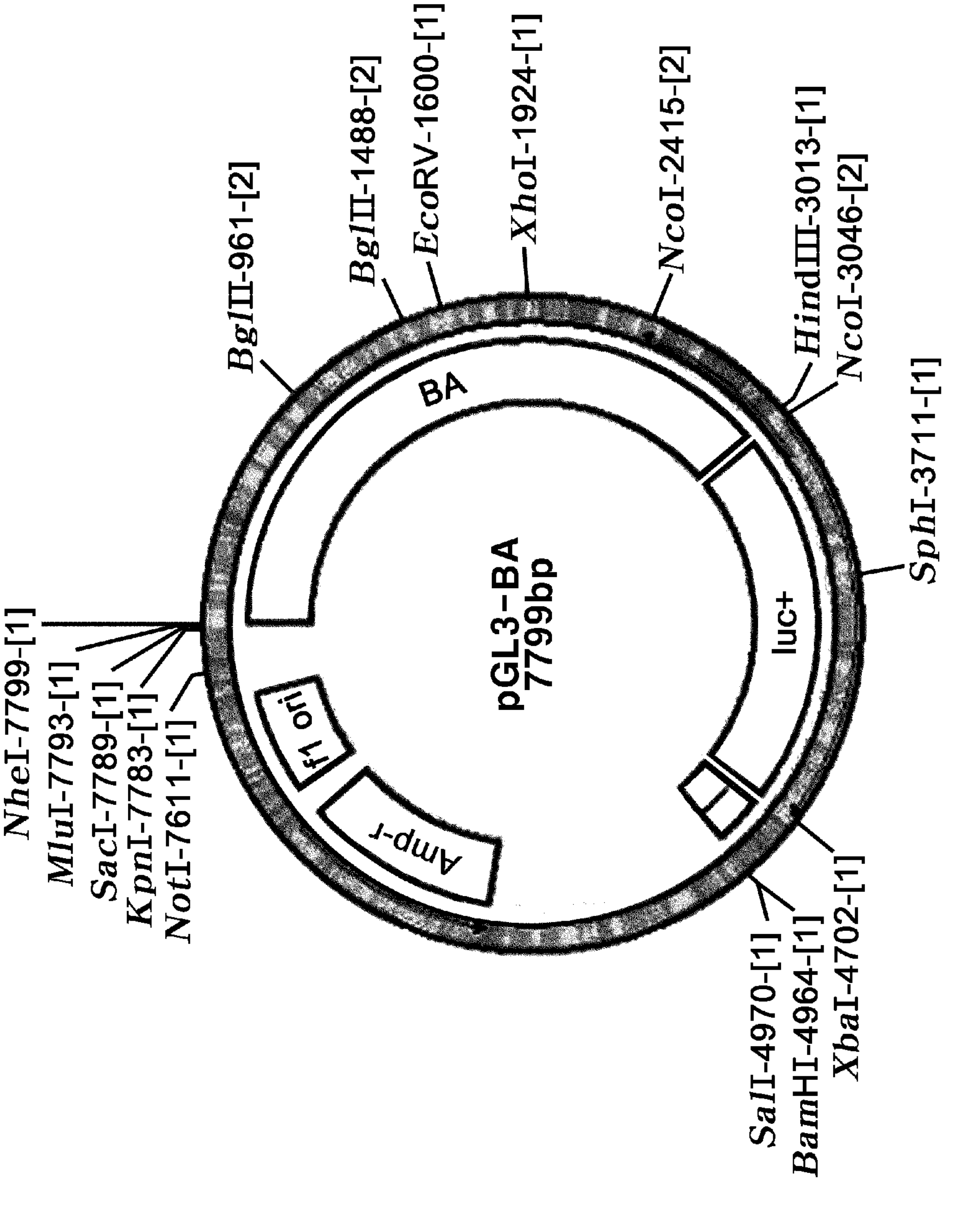
FIG. 3 shows the structure of a pGL3-BA vector, in which a β-actin promoter is introduced into a pGL3-Basic vector.
Figure 5:
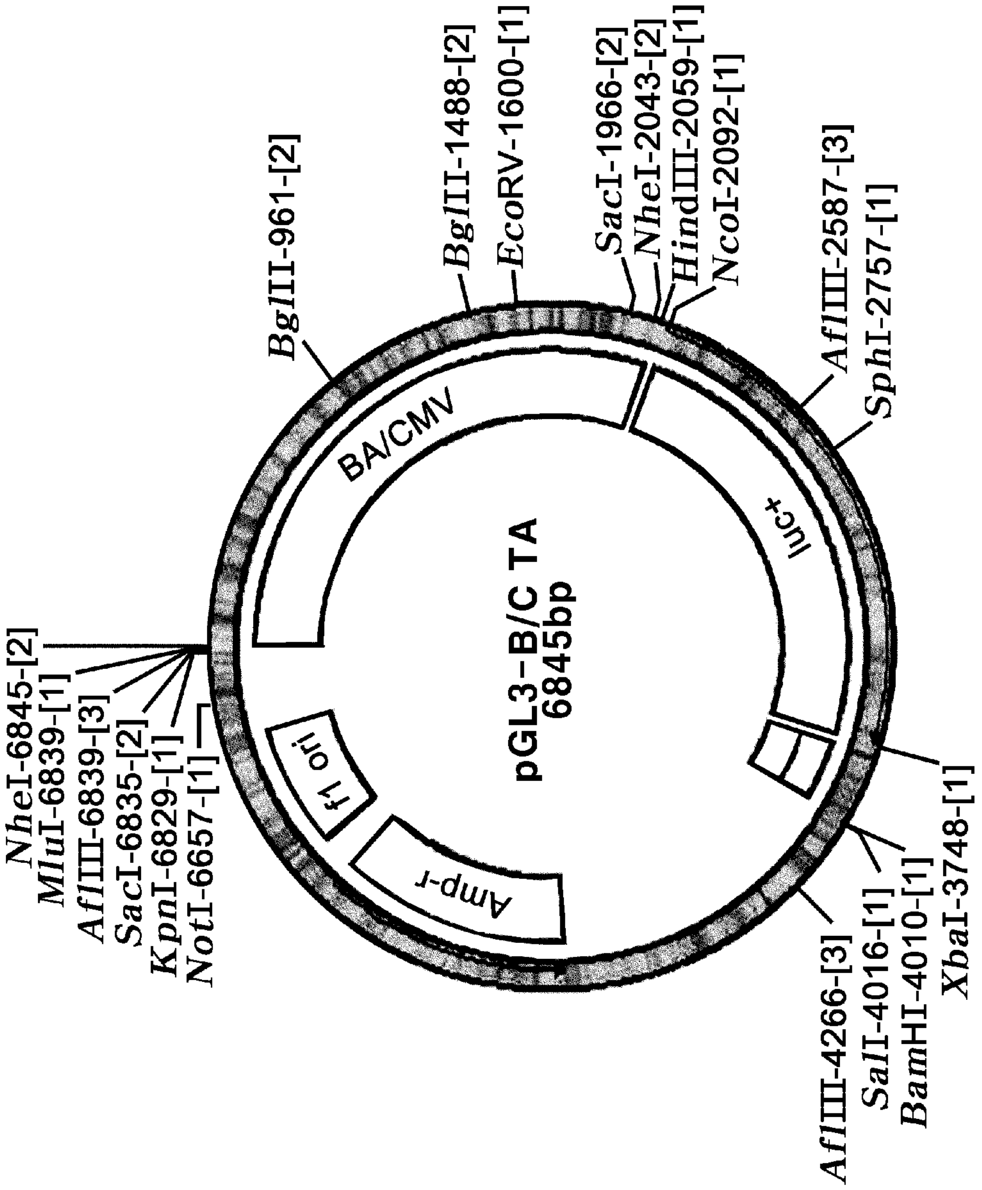
FIG. 5 shows the structure of a pGL3-B/$C_{TA}$ vector, in which a hybrid promoter comprising a β-actin promoter (1.9 kb) and a TATA box region of a CMV promoter (130 bp) is introduced into a pGL3-Basic vector.
Figure 6:
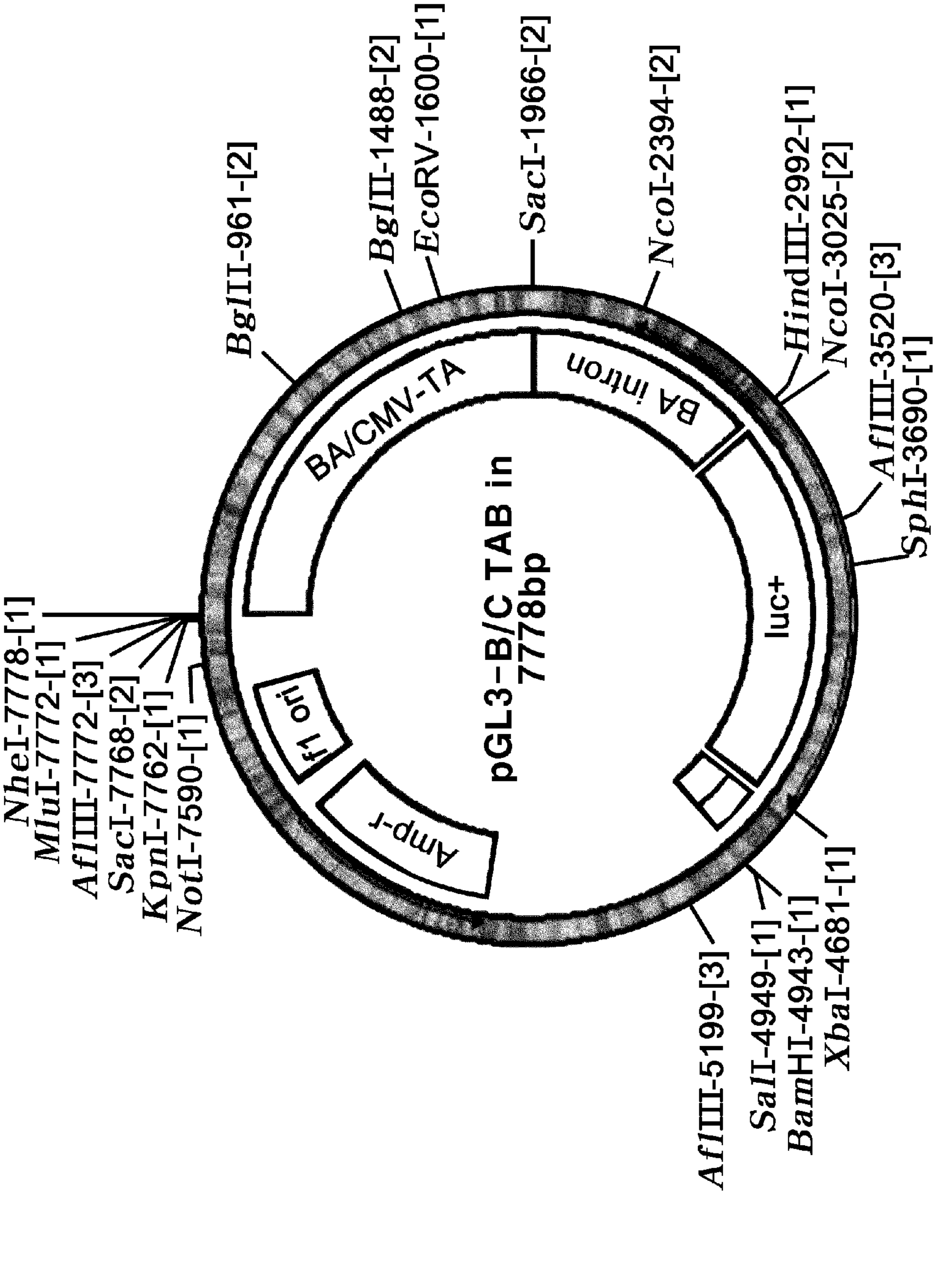
FIG. 6 shows the structure of a pGL3-B/$C_{TA}$/$B_{in}$ vector, in which a hybrid promoter comprising a β-actin promoter (1.9 kb), a TATA box region of a CMV promoter (130 bp) and a β-actin intron region is introduced into a pGL3-Basic vector.
Figure 7:
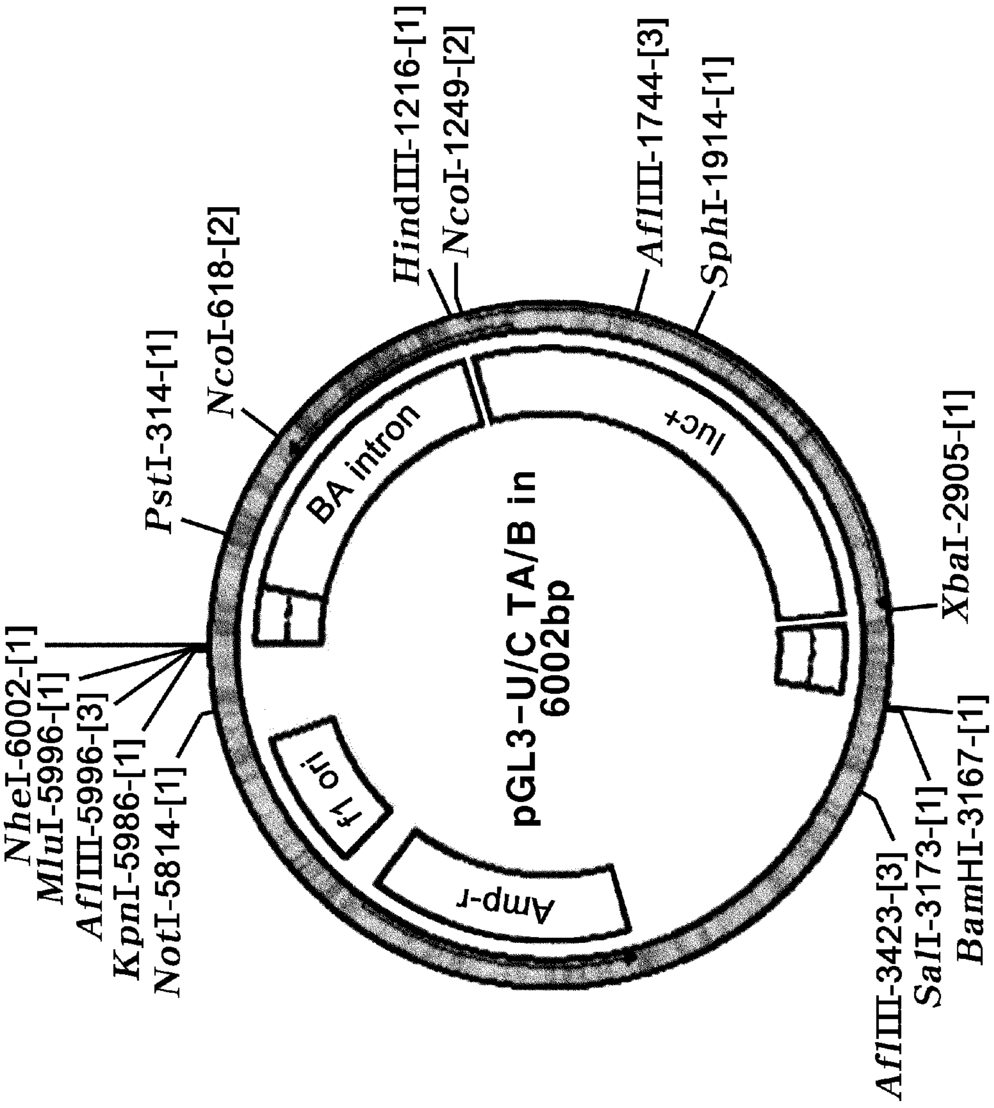
FIG. 7 shows the structure of a pGL3-U/$C_{TA}$/$B_{in}$ vector, in which a hybrid promoter comprising a β-actin promoter (150 bp), a TATA box region of a CMV promoter (130 bp) and a β-actin intron region is introduced into a pGL3-Basic vector.

To develop a hybrid promoter suitable for induction of immune responses in vivo with increasing an expression level of a target gene, the present invention has prepared the following recombinant vectors by combinations of various promoter/enhancer sequences, poly (A) sequences and intron sequences:

pGL3-Basic: f1 ori, synthetic poly (A)/transcriptional pause site, multiple cloning site (MCS), liciferase reporter gene ($luc^+$), SV40 late polyadenylation signal, $Amp^r$ (see FIG. 1)

pGL3-Promoter (SV40): f1 ori, synthetic poly (A)/transcriptional pause site, MCS, SV40 promoter, luciferase gene ($luc^+$), SV40 late polyadenylation signal, ampicillin resistance gene ($Amp^r$) (see FIG. 2)

pGL3-BA: f1 ori, synthetic poly (A)/transcriptional pause site, MCS, β-actin promoter, $luc^+$, SV40 late polyadenylation signal, $Amp^r$ (see FIG. 3)

pGL3-B/$C_{TA}$: f1 ori, synthetic poly (A)/transcriptional pause site, MCS, hybrid promoter of β-actin promoter (1.9 kb) and TATA box region (130 bp) of CMV promoter, $luc^+$, SV40 late polyadenylation signal, $Amp^r$ (see FIG. 5)

pGL3-B/$C_{TA}$/$B_{1n}$: f1 ori, synthetic poly (A)/transcriptional pause site, MCS, hybrid promoter of β-actin promoter (1.9 kb) and TATA box region (130 bp) of CMV promoter, β-actin intron, $luc^+$, SV40 late polyadenylation signal, $Amp^r$ (see FIG. 6)

pGL3-U/$C_{TA}$/$B_{1n}$: f1 ori, synthetic poly (A)/transcriptional pause site, MCS, hybrid promoter of U20114 region (150 bp) of β-actin promoter and TATA box region (130 bp) of CMV promoter, β-actin intron, $luc^+$, SV40 late polyadenylation signal, $Amp^r$ (see FIG. 7)

pGL3-$C_{eh}$/U/$C_{TA}$/$B_{in}$: f1 ori, synthetic poly (A)/transcriptional pause site, MCS, CMV enhancer, hybrid promoter of U20114 region (150 bp) of β-actin promoter and TATA box region (130 bp) of CMV promoter, β-actin intron, $luc^+$, SV40 late polyadenylation signal, $Amp^r$ (see FIG. 8)

In order to examine the capability to induce the expression of a target protein, each of the recombinant vectors described above was transformed into CHO cells, and then expression levels of a luciferase gene inserted as a reporter gene were compared. A pGL3-Basic vector, which has a basic structure of the vector used in the present invention and dispenses with the promoter and enhancer sequences according to the present invention, was used as a control group (see FIG. 1). As a result, the luciferase expression level was remarkably increased in the recombinant vector having a hybrid promoter of a CMV enhancer, 150 bp of a β-actin promoter, a CMV promoter and a β-actin intron (pGL3-$C_{eh}$/U/$C_{TA}$/$B_{in}$ of FIG. 8), compared to the recombinant vector having a β-actin promoter (pGL3-BA of FIG. 3), the recombinant vector having a hybrid promoter of 1.9 kb of a β-actin promoter and a TATA box region of a CMV promoter, (pGL3-B/$C_{TA}$ of FIG. 5), the recombinant vector having a hybrid promoter of 1.9 kb of a β-actin promoter, a TATA box region of a CMV promoter, and a β-actin intron region (pGL3-B/$C_{TA}$/$B_{in}$ of FIG. 6), and the recombinant vector having a hybrid promoter of 150 bp of a β-actin promoter, a TATA box region of a CMV promoter, and a β-actin intron region (pGL3-U/$C_{TA}$/$B_{in}$ of FIG. 7) (see Tables 1 and 2, and FIG. 9).

Therefore, it has been found that when a target protein-encoding gene, instead of the luciferase gene, is inserted into the recombinant vector of the present invention, the transcription and expression of the target gene are increased by the activity of the hybrid promoter of the present invention, thereby mass-producing the target protein.

In still another embodiment, the present invention provides a transformant that is transformed with the recombinant vector.

As used herein, the term "transformation" refers to introduction of a nucleic acid into host cells. As a transformation method, any technique for introducing DNA into host cells can be used, including various well-known techniques, such as electroporation, calcium phosphate co-precipitation, retroviral infection, microinjection, DEAE-dextran and cationic liposome, but is not limited thereto.

As used herein, the term "transformant" refers to the whole or a part of an organism, such as a cell, into which a foreign DNA is introduced by transformation. Examples of a host cell may include prokaryotic cells, yeast, animal cells, plant cells, insect cells and the like, preferably animal cells or animal cell-derived cells, and most preferably Chinese Hamster Ovary (CHO) cells. Transformation of CHO cells with a target gene along with an amplifiable gene such as dihydrofolate reductase (DHFR) or glutamine synthetase (GS) offers effective platforms for expression of the required proteins. The DHFR system is routinely used with CHO cells deficient in the DHFR activity ($DHFR^-$). The target gene is delivered to the cells along with the DHFR marker gene, usually on the same plasmid vector. Exposure of the transformed cells to the DHFR enzyme inhibitor, methotrexate (MTX) promotes amplification of the DHFR and the cotransformed target gene. MTX treatment enhances specific protein production following an increased gene copy number.

In still another embodiment, the present invention provides to a pharmaceutical composition comprising the recombinant vector or the transformant as an effective ingredient, and a pharmaceutically acceptable carrier. The composition of the present invention is administered in a pharmaceutically effective amount.

As used herein, the term "pharmaceutically effective amount" in the context of the effective ingredient refers to an amount sufficient for exhibiting intended efficacy in a reasonable benefit/risk ratio so as to be applicable to medical treatment.

As used herein, the term "pharmaceutically acceptable carrier" refers to a material which is used for production of a pharmaceutical agent or an agricultural chemical (e.g., an animal drug), and has no adverse effect on effective ingredients. Any pharmaceutically acceptable carrier known in the art may be used in the pharmaceutical composition of the present invention.

For oral administration, the pharmaceutically acceptable carrier may include a binder, a lubricant, a disintegrator, an excipient, a solubilizer, a dispersing agent, a stabilizer, a suspending agent, a coloring agent and a perfume. For injectable administration, the pharmaceutically acceptable carrier may include a buffering agent, a preserving agent, an analgesic, a solubilizer, an isotonic agent and a stabilizer. For topical administration, the pharmaceutically acceptable carrier may include a base, an excipient, a lubricant, and a preserving agent.

The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable administration, the pharmaceutical composition may be formulated into an ampule as a single-dose dosage form or a unit dosage form, such as a multidose container. The pharmaceutical composition may be also formulated into solutions, suspensions, tablets, pills, capsules and long-acting preparations.

On the other hand, examples of the carrier, excipient and diluent suitable for the pharmaceutical composition of the present invention may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate and mineral oils. In addition, the pharmaceutical composition of the present invention may further include fillers, anti-coagulating agents, lubricants, humectants, perfumes and antiseptics.

The pharmaceutical composition of the present invention may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but are not limited thereto.

However, since peptides are digested upon oral administration, the effective ingredient of the pharmaceutical composition for oral administration should be coated or formulated for protection against degradation in the stomach. Preferably, the pharmaceutical composition of the present invention may be administered in an injectable form. In addition, the pharmaceutical composition of the present invention may be administered using a certain apparatus capable of transporting the effective ingredient into a target cell.

The administration frequency and dose of the pharmaceutical composition of the present invention can be determined by several related factors including the types of diseases to be treated, administration routes, the patient's age, gender, weight and severity of the illness, as well as by the types of the drug as an effective ingredient. The composition of the present invention may be administered alone or in combination with other therapeutic agent, and either sequentially or simultaneously, in a single dose or multiple doses. Considering all of the above factors, a minimum amount to achieve maximum efficacy without side effects can be readily determined by those skilled in the art.

In still another embodiment, the present invention provides a method for preparing a target protein, comprising the steps of:

1) culturing the transformant of the present invention;

2) inducing the expression of a target protein from the transformant; and 3) harvesting the expressed target protein from the transformant or the culture solution thereof.

As used herein, the term "target protein" includes antibodies, enzymes, cytokines, lymphokines, adhesion molecules, receptors and the derivatives or fragments thereof, but is not limited thereto. Generally, all kinds of polypeptides which act as agonists or antagonists and/or have therapeutic or diagnostic applications can be used as a target protein. Other target proteins include, for example, anti-apoptotic proteins, chaperones, metabolic enzymes, glycosylation enzymes and the derivatives or fragments thereof, but are not limited thereto.

As used herein, the term "polypeptide" refers to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, for instance Creighton, (1993), Posttranslational Covalent Modification of Proteins, W.H. Freeman and Company, New York B. C. Johnson, Ed., Academic Press, New York 1-12; Seifter, et al., (1990) Meth Enzymol 182:626-646; Rattan et al., (1992) Ann N Y Acad Sci 663:48-62). Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

Examples of the target protein prepared according to the method of the present invention may include, but are not limited to, human growth hormones, growth hormone release hormones, growth hormone release peptides, interferons and interferon receptors (e.g., interferon-alpha, -beta and -gamma, Type I soluble interferon receptor, etc.), granulocyte-colony stimulating factors (G-CSFs), granulocytemacrophage-colony stimulating factors (GM-CSFs), glucagons-like peptides (GLP-1, etc.), G-protein-coupled receptors, interleukins (e.g., IL-1 receptor, IL-4 receptor, etc.), enzymes (e.g., glucocerebrosidase, iduronate-2-sulfatase, alpha-galactosidase-A, agalsidase alpha, beta- or alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin- or cytokine-binding proteins (e.g., IL-18 bp, TNF-binding proteins, etc.), macrophage activating factors, macrophage peptides, B cell factors, T cell factors, protein A, allergy inhibitors, cell necrosis glycoprotein, immune toxins, lymph toxins, tumor necrosis factors, tumor suppressing factors, transitional growth factors, alpha-1 antitrypsin, albumin, alpha-lactalbumin, apolipoprotein-E, erythropoietin, highly glycosylated erythropoietin, angiopoietin, hemoglobin, thrombin, thrombin receptor activating peptides, thrombomodulin, blood factor VII, blood factor VIIa, blood factor VIII, blood factor IX, blood factor XIII, plasminogen activating factor, fibrin-binding peptides, urokinases, streptokinases, hirudin, protein C, C-reactive proteins, rennin inhibitors, collagenase inhibitors, superoxide dismutases, leptin, platelet-originated growth factor, epithelial growth factor, epidermal growth factor, angiostatin, angiotensin, myelopoiesis growth factor, myelopoiesis stimulating factor, calcitonin, insulin, atriopeptin, cartilage inducer, elcatonin, joint tissue activating factor, tissue factor pathway inhibitor, follicle stimulating hormone, progesterone forming hormone, progesterone forming hormone releasing hormone, nerve growth factors (e.g., nerve growth factor, cilliary neurotrophic factor, axogenesis factor-1, brain-natriuretic peptide, glial derived neurotrophic factor, netrin, neurophil inhibitor factor, neurotrophic factor, neuturin, etc.), parathormone, relaxin, cycretin, somatomedine, insulin-like growth factor, adrenocortical hormones, glucagons, cholecystokynine, pancreatic polypeptides, gastrin releasing peptide, corticotropin releasing factor, thyroid stimulating hormone, autotaxin, lactoferrin, myostatin, receptors (e.g., TNFR (P75), TNFR(P55), IL-1 receptor, VEGF receptor, B cell activating factor receptor, etc.), receptor antagonists (e.g., IL1-Ra, etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', $F(ab')_2$ and Fd), virus-originated vaccine antigens. The antibody fragments include Fab, Fab', $F(ab')_2$, Fd or scFv, which is capable of binding to a specific antigen, and preferably Fab'.

Production systems for the target proteins described above may be in vitro or in vivo. In vitro production systems may employ the use of eukaryotic or prokaryotic cells. For example, the target protein can be obtained by culturing the transformant of the present invention in vitro. The cultivation of the transformant may be performed according to conventional methods in the art, and the conditions such as temperature, time and pH of a medium may be suitably controlled. Culture media used for the cultivation need to meet the requirements for growth of particular strains in an appropriate manner. Culture media for various strains are disclosed in, for example, "Manual of Methods for General Bacteriology" from American Society for Bacteriology (Washington D.C., USA, 1981). A carbon source for the culture media may be sugar and carbohydrate (e.g., glucose, sucrose, lactose, fructose, maltose, molasses, starch and cellulose), oil and fat (e.g., soybean oil, sunflower oil, peanut oil and coconut oil), a fatty acid (e.g., palmitic acid, stearic acid and linolenic acid), an alcohol (e.g., glycerol and ethanol), and an organic acid (e.g., acetic acid). The carbon sources may be used alone or in a mixture. A nitrogen source may also be a nitrogen-containing organic compound (e.g., peptone, yeast extract, meat extract, malt extract, corn steep liquor, soy meal and urea) or an inorganic compound (e.g., ammonium sulfate, ammonium chloride, ammonium phosphate, ammonium carbonate and ammonium nitrate). The nitrogen source may be used alone or in a mixture. A phosphorous source may be potassium dihydrogen phosphate, dipotassium hydrogen phosphate or its sodium salt thereof. In addition, the culture media should contain a metal salt (e.g., magnesium sulfate or iron sulfate) essential for growth. Finally, the culture medium may further include substances essential for growth such as amino acids and vitamins in addition to the above mentioned substances. Suitable precursors may be also added to the culture media. Those components of culture media may be added to the culture media on a batch or on a continuous basis during the cultivation.

The pH of the culture medium may be adjusted with a basic compound (e.g., sodium hydroxide, potassium hydroxide or ammonia), or an acidic compound (e.g., phosphoric acid or sulfuric acid). A defoaming agent such as fatty acid polyglycol ester may be added to prevent the formation of bubbles. An aerobic state may be maintained by injecting oxygen or oxygen-containing gas (e.g., air) into the culture medium.

For example, liquid culture media for animal cells may include DMEM, MEM, RPM11640, IMDM, F10 medium, and F12 medium. The culture media may include serum supplements such as fetal calf serum (FCS), or may be serum-free culture media. Furthermore, a transactivator may be added to the media. The cultivation is preferably performed at approximately pH 6.0 to 8.0. The cultivation is typically carried out at approximately 30 to 40° C. for approximately 15 to 200 hours. If required, the medium may be changed, aerated or stirred.

Since culture conditions vary depending on the cell type used, those skilled in the art can appropriately determine suitable conditions. For example, CHO cells may be cultured under a $CO_2$ atmosphere of 0 to 40%, preferably 2 to 10%, at a temperature of 30 to 39° C., preferably 37° C. for 1 to 14 days.

Various culture apparatuses can be used for animal cells, and exemplified by fermentation tank-type tank culture apparatuses, airlift-type culture apparatuses, culture flask-type culture apparatuses, spinner flask-type culture apparatuses, microcarrier-type culture apparatuses, flow tank-type culture apparatuses, hollow fiber-type culture apparatuses, roller bottle-type culture apparatuses, packed bed-type culture apparatuses or the like.

Meanwhile, in vivo production systems may include, for example, production systems using animals or plants. A DNA of interest can be introduced into such an animal or plant, and the polypeptide produced in the animal or plant in vivo can be collected.

MODE FOR THE INVENTION

Hereinafter, the present invention will be described in more detail with reference to Examples. However, these Examples are for illustrative purposes only, and the invention is not intended to be limited by these Examples.

Example 1

General Molecular Biological Techniques

Methods generally used in molecular biology, such as restriction enzyme treatment, agarose gel electrophoresis, gel extraction, plasmid DNA purification, polymerase chain reaction (PCR), DNA fragment ligation and *E. coli* transformation, were performed according to the methods described in the literature with minor modifications (Sambrook J et al., 2001 Molecular cloning: A laboratory manual, 2nd edition. Cold Spring Harbor Laboratory Press, Cold Spring Harbor, N.Y.).

Example 2

Preparation of Plasmid Vectors

<2-1> Preparation of pGL3-BA Vector

PCR was performed using a total genomic DNA obtained from CHO cells as a template and a primer pair of SEQ ID NOs: 1 and 2 to amplify a β-actin promoter gene, and thus amplified PCR product was treated with restriction enzymes NheI and HindIII. The resulting β-actin promoter DNA fragment (3.0 kb) was inserted into a pGL3-Basic vector (Promega) treated with the same restriction enzymes, to thereby prepare a pGL3-BA vector (FIG. 3). Here, PCR was performed under the following conditions: initial denaturation at 94° C. for 5 minutes; 25 cycles of denaturation at 94° C. for 1 minute, annealing at 55° C. for 1 minute and polymerization at 72° C. for 3.5 minutes; and final elongation at 72° C. for 7 minutes.

```
5'-BA 1_F(NheI):
                                        (SEQ ID NO: 1)
5'-CAG CTA GCG GGA CCA AGA CAG AAC CAT AA-3'

3'-BA 4_R(HindIII):
                                        (SEQ ID NO: 2)
5'-GTA AGC TTC GGC GAA CTA TAT CAG GGC A-3'
```

As shown in FIG. 3, the prepared pGL3-BA vector includes f1 ori, synthetic poly (A)/transcriptional pause site, MCS, β-actin promoter, luc$^+$, SV40 late polyadenylation signal and Amp resistance gene.

<2-2> Preparation of pGL3-B/$C_{TA}$ Vector

Figure 4:
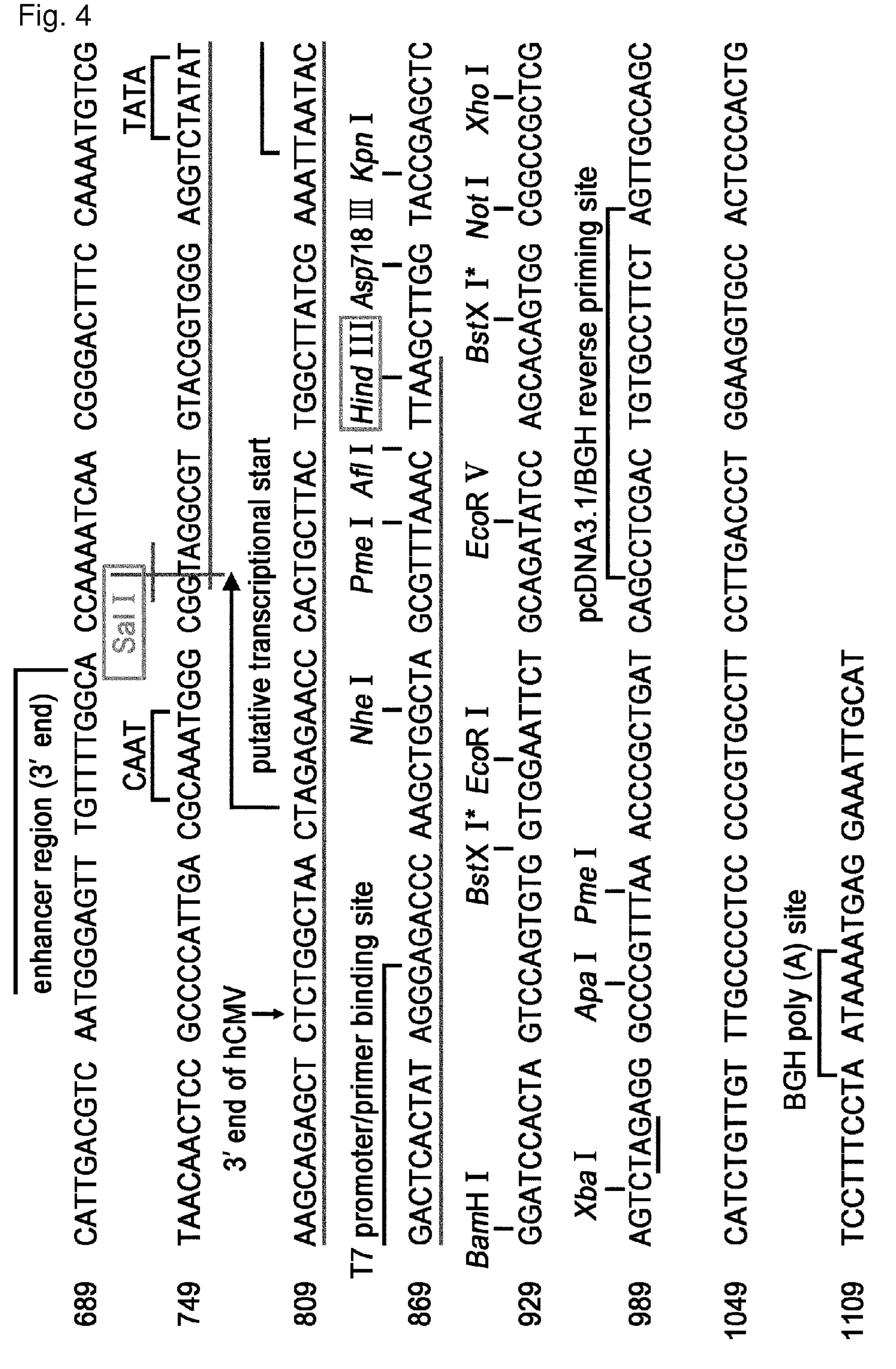
FIG. 4 shows a TATA box region of a CMV promoter of a pcDNA3.1 vector (SEQ ID NO:14) used in the present invention.

PCR was performed using a pcDNA3.1 vector (Invitrogen) as a template and a primer pair of SEQ ID NOs: 4 and 5 to amplify a TATA box region (130 bp) of a CMV promoter (FIG. 4), and thus amplified PCR product was treated with restriction enzymes SalI and HindIII. The resulting DNA fragment of the TATA box region was inserted into the pGL3-BA vector treated with restriction enzymes XhoI and HindIII, to thereby prepare a pGL3-B/$C_{TA}$ vector (FIG. 5). The resulting vector pGL3-B/$C_{TA}$ does not have SalI and XhoI restriction sites. Here, PCR was performed under the following conditions: initial denaturation at 94° C. for 5 minute; 25 cycles of denaturation at 94° C. for 1 minute, annealing at 55° C. for 1 minute and polymerization at 72° C. for 2.5 minute; and final elongation at 72° C. for 7 minute.

```
5-CMV TA_F(SalI):
                                        (SEQ ID NO: 4)
5'-CAG TCG ACT AGG CGT GTA CGG TGG GAG-3'

3'-BGH reverse priming site:
                                        (SEQ ID NO: 5)
5'-TAG AAG GCA CAG TCG AGG-3'
```

As shown in FIG. 5, the prepared pGL3-B/$C_{TA}$ vector includes f1 ori, synthetic poly (A)/transcriptional pause site, MCS, a hybrid promoter of a β-actin promoter (1.9 kb) and a TATA box region (130 bp) of a CMV promoter, luc$^+$, SV40 late polyadenylation signal and Amp resistance gene.

<2-3> Preparation of pGL3-B/$C_{TA}$/$B_{in}$ Vector

PCR was performed using a pGL3-BA vector prepared in Example 2-1 as a template and a primer pair of SEQ ID NOs: 6 and 2 to amplify a β-actin intron region, and thus amplified PCR product was treated with restriction enzymes SacI and HindIII, to thereby obtain a DNA fragment (1 kb) of β-actin intron. In addition, the pGL3-B/$C_{TA}$ vector prepared in Example 2-2 was treated with restriction enzymes EcoRV and SacI, to thereby obtain a DNA fragment (370 bp) of TATA box region. After the pGL3-B/$C_{TA}$ vector was treated with restriction enzymes EcoRV and HindIII, the DNA fragment (1 kb) of β-actin intron and the DNA fragment (370 bp) of TATA box region were inserted into the vector, to thereby prepare a pGL3-B/$C_{TA}$/$B_{in}$ vector (FIG. 6). The resulting vector pGL3-B/$C_{TA}$/$B_{in}$ has two SacI restriction sites. Here, PCR was performed under the following conditions: initial denaturation at 94° C. for 5 minute; 25 cycles of denaturation at 94° C. for 1 minute, annealing at 55° C. for 1 minute and polymerization at 72° C. for 3.5 minute; and final elongation at 72° C. for 7 minute.

```
5'-BA-int(SacI):
                                        (SEQ ID NO: 6)
5'-CAA GAG CTC TCT GGC TAA CTG AGC ACA GGC CTT

TC-3'

3'-BA 4_R(HindIII):
                                        (SEQ ID NO: 2)
5'-GTA AGC TTC GGC GAA CTA TAT CAG GGC A-3'
```

As shown in FIG. 6, the prepared pGL3-B/$C_{TA}$/$B_{in}$ vector includes f1 ori, synthetic poly (A)/transcriptional pause site, MCS, a hybrid promoter of a β-actin promoter (1.9 kb) and a TATA box region (130 bp) of a CMV promoter, a β-actin intron, luc$^+$, SV40 late polyadenylation signal and Amp resistance gene.

<2-4> Preparation of pGL3-U/$C_{TA}$/$B_{in}$ Vector

PCR was performed using the pGL3-B/$C_{TA}$/$B_{in}$ vector prepared in Example 2-3 as a template and a primer pair of SEQ ID NOs: 3 and 2 to amplify a DNA fragment covering a U20114 region of a β-actin promoter, a TATA box region of a CMV promoter and a β-actin intron, and thus amplified PCR product was treated with restriction enzymes NheI and HindIII. The resulting DNA fragment was inserted into the pGL3-Basic vector treated with the same restriction enzymes, to thereby prepare a pGL3-U/$C_{TA}$/$B_{in}$ vector (FIG. 7). Here, PCR was performed under the following conditions: initial denaturation at 94° C. for 5 minute; 25 cycles of denaturation at 94° C. for 1 minute, annealing at 55° C. for 1 minute and polymerization at 72° C. for 1.5 minute; and final elongation at 72° C. for 7 minute.

```
5'-U20114_(NheI):
                                        (SEQ ID NO: 3)
5'-CAC GCT AGC TCT CTC TTT TTT TTT TTT TAT-3'

3'-BA 4_R(HindIII):
                                        (SEQ ID NO: 2)
5'-GTA AGC TTC GGC GAA CTA TAT CAG GGC A-3'
```

As shown in FIG. 7, the prepared pGL3-U/$C_{TA}$/$B_{in}$ vector includes f1 ori, synthetic poly (A)/transcriptional pause site, MCS, a hybrid promoter of a U20114 region of a β-actin promoter and a TATA box region (130 bp) of a CMV promoter, a β-actin intron, luc$^+$, SV40 late polyadenylation signal and Amp resistance gene.

<2-5> Preparation of pGL3-$C_{eh}$/U/$C_{TA}$/$B_{in}$ Vector

PCR was performed using a pcDNA3.1 vector (Invitrogen) as a template and a primer pair of SEQ ID NOs: 7 and 8 to amplify an enhancer region of a CMV promoter, and thus amplified PCR product was treated with restriction enzymes MluI and NheI. The resulting DNA fragment of the CMV enhancer was inserted into the pGL3-U/$C_{TA}$/$B_{in}$ vector treated with the same restriction enzymes, to thereby prepare a pGL3-$C_{eh}$/U/$C_{TA}$/$B_{in}$ vector (FIG. 8). Here, PCR was performed under the following conditions: initial denaturation at 94° C. for 5 minute; 25 cycles of denaturation at 94° C. for 1 minute, annealing at 55° C. for 1 minute and polymerization at 72° C. for 1 minute; and final elongation at 72° C. for 7 minute.

```
5'-CMV En_F(MluI):
                                        (SEQ ID NO: 7)
5'-CAG ACG CGT TGA CAT TGA TTA TTG ACT-3'

3'-CMV En_R(NheI):
                                        (SEQ ID NO: 8)
5'-CAG GCT AGC AGT TGT TAC GAC ATT TTG-3'
```

As shown in FIG. 8, the prepared pGL3-U/$C_{TA}$/$B_{in}$ vector includes f1 ori, synthetic poly (A)/transcriptional pause site, MCS, a hybrid promoter of a CMV enhancer, a U20114 region of a β-actin promoter and a TATA box region (130 bp) of a CMV promoter, a β-actin intron, luc$^+$, SV40 late polyadenylation signal and Amp resistance gene.

Example 3

In Vitro Efficacy Test of Plasmid Vectors

Each of the recombinant vectors prepared in Example 2 was transformed into CHO cells, and then luciferase expression levels were examined by ELISA.

First, the recombinant vector was introduced into CHO cells using lipofectamine (Invitrogen). Specifically, CHO cells were maintained in a DMEM medium (Dulbecco's modified Eagles's medium, GIBCO-BRL) supplemented with heat-inactivated 10% FBS (Fetal bovine serum, GIBCO-BRL). Each of the recombinant vectors prepared in Example 2 and a pCH110 vector harboring n-gal were cotransformed into the cultured CHO cells. One day before transformation, the CHO cells were cultured in a 24-well plate (Falcon) at a density of $6\times10^4$ cells per well.

Meanwhile, Tube 1 (reaction amount for 1 well) containing each 500 ng of the recombinant vectors prepared in Example 2, 150 ng of the pCH110 vector for β-gal correction, 0.83 μl of Plus Reagent, and 23.92 μl of Opti-MEM, and Tube 2 (reaction amount for 1 well) containing 1.25 μl of lipofectamine and 30 μl of Opti-MEM were left at room temperature for 15 minutes, respectively. Then, two tubes were mixed with each other, followed by reacting at room temperature for further 15 minutes. The medium of the well plate containing the cultured CHO cells was replaced with 200 μl of Opti-MEM, and then 60 μl of the mixture was added to each well. The well plate was then incubated at 5% $CO_2$, 37° C. for 3 hours. After incubation, 260 μl of DMEM supplemented with 20% FBS was added to each well, and cultivation was performed for further 2 days.

After 2 days, the medium was removed from each well, and the well plate was washed with 300 μl of PBS. 100 μl of 1 Reporter Lysis Buffer (Promega) was added to each well, followed by freezing the well plate and thawing it at 37° C. The reaction solution was gently shaken at room temperature, and then each 20 μl was transferred to an analysis plate to perform a luciferase assay and a β-gal assay. The β-gal assay was performed so as to determine whether transformation had occurred uniformly, and the luciferase assay results were corrected by the β-gal assay results.

As shown in the following Tables 1 and 2, and FIG. 10, compared to the known pGL3-BA vector, the pGL3-$C_{eh}$/U/$C_{TA}$/$B_{in}$ vector showed an increased luciferase expression level, and the pGL3-B/$C_{TA}$/$B_{in}$ and pGL3-U/$C_{TA}$/$B_{in}$ vectors showed a similar or slightly low luciferase expression level. In contrast, the pGL3-B/$C_{TA}$ vector showed a lower luciferase expression level than the pGL3-BA vector. However, when the β-gal assay was performed by co-transformation with the pCH110 vector for correction in every experiment, it showed lower β-gal values (0.7-3), compared to the pGL3-$C_{eh}$/U/$C_{TA}$/$B_{in}$ vector (near 3) showing the high luciferase expression level.

TABLE 1

| | Luminescent | | β-gal | | β-gal corrected | | LUC | |
|---|---|---|---|---|---|---|---|---|
| First round | Sample 1 | Sample 2 | Sample 1 | Sample 2 | Sample 1 | Sample 2 | Average corrected | Stdev |
| 1 pGL3-Basic | 1763 | 1550 | 2.890 | 3.214 | 610 | 482 | 546 | 90 |
| 2 pGL3-promoter(SV40) | 3356 | 3374 | 2.960 | 3.107 | 1134 | 1086 | 1110 | 34 |
| 3 pGL3-BA | 12557 | 12811 | 3.106 | 3.254 | 4043 | 3937 | 3990 | 75 |
| 4 pGL3-B/$C_{TA}$ | 3533 | 3902 | 3.151 | 3.312 | 1121 | 1178 | 1150 | 40 |
| 5 pGL3-B/$C_{TA}$/$B_{in}$ | 13577 | 13566 | 3.152 | 3.126 | 4307 | 4340 | 4324 | 23 |
| 6 pGL3-U/$C_{TA}$/$B_{in}$ | 13501 | 13499 | 3.197 | 3.368 | 4223 | 4008 | 4116 | 152 |
| 7 pGL3-$C_{eh}$/U/$C_{TA}$/$B_{in}$ | 13469 | 13439 | 1.893 | 2.013 | 7115 | 6676 | 6896 | 310 |

TABLE 2

| | Luminiscent | | β-gal | | β-gal corrected | | LUC | |
|---|---|---|---|---|---|---|---|---|
| Second round | Sample 1 | Sample 2 | Sample 1 | Sample 2 | Sample 1 | Sample 2 | Average corrected | Stdev |
| 1 pGL3-Basic | 3346 | 2841 | 3.300 | 3.254 | 1014 | 873 | 944 | 100 |
| 2 pGL3-promoter(SV40) | 3356 | 3096 | 2.451 | 2.443 | 1369 | 1267 | 1318 | 72 |
| 3 pGL3-BA | 12557 | 13567 | 3.336 | 3.235 | 3764 | 4194 | 3979 | 304 |
| 4 pGL3-B/$C_{TA}$ | 3533 | 4520 | 3.269 | 3.124 | 1081 | 1447 | 1264 | 259 |
| 5 pGL3-B/$C_{TA}$/$B_{in}$ | 13577 | 13569 | 3.286 | 3.166 | 4132 | 4286 | 4209 | 109 |
| 6 pGL3-U/$C_{TA}$/$B_{in}$ | 13586 | 13558 | 2.821 | 2.886 | 4816 | 4698 | 4757 | 84 |
| 7 pGL3-$C_{eh}$/U/$C_{TA}$/$B_{in}$ | 13531 | 13464 | 1.241 | 1.307 | 10903 | 10301 | 10602 | 426 |

*Luminescent: represents luminescence values expressed by luciferase gene inserted in vector
*β-gal: represents galactosidase expression level
*β-gal corrected: represents corrected values for comparison of galactosidase expression level of each promoter
*LUC average corrected: represents luciferase expression level corrected by average
*Stdev: represents standard deviation of luciferase expression level

INDUSTRIAL APPLICABILITY

The present invention provides a novel promoter that is optimized for the production of an antibody or a DNA vaccine. When a variety of target genes are inserted into a recombinant vector including the hybrid promoter of the present invention, transcription and expression of the target genes can be improved. Therefore, the recombinant vector including the hybrid promoter of the present invention can be utilized for the development of antibody or DNA vaccine.

The invention claimed is:

1. A hybrid promoter comprising a cytomegalovirus (CMV) enhancer having the nucleotide sequence of SEQ ID NO:13, a β-actin promoter having the nucleotide sequence of SEO ID NO:9 or SEQ ID NO:10, a TATA box of a CMV promoter having the nucleotide sequence of SEQ ID NO:11, and a β-actin intron having the nucleotide sequence of SEQ ID NO:12, wherein the CMV enhancer, β-actin promoter, CMV promoter TATA box and β-actin intron are operably linked to each other in a 5' to 3' direction.

2. A recombinant vector comprising the hybrid promoter of claim 1 and a target protein-encoding gene operably linked thereto.

3. The recombinant vector according to claim 2, further comprising one or more expression regulatory elements selected from the group consisting of a replication origin, a selectable marker, a reporter gene, a terminator and combinations thereof.

4. The recombinant vector according to claim 3, wherein the selectable marker is a drug resistance gene.

5. The recombinant vector according to claim 4, wherein the drug resistance gene is a gene resistant to antibiotics selected from the group consisting of ampicillin, streptomycin, gentamicin, kanamycin, hygromycin, tetracycline, chloramphenicol and neomycin.

6. The recombinant vector according to claim 3, wherein the reporter gene is a gene encoding a protein selected from the group consisting of green fluorescent protein (GFP), cyan fluorescent protein (CFP), yellow fluorescent protein (YFP), red fluorescent protein (dsRFP), luciferase (Luc), chloramphenicol acetyltransferase (CAT), 13-galactosidase (LacZ) and 13-glucuronidase (Gus).

7. An isolated transformant in which the recombinant vector of claim 2 is introduced into a host cell.

8. The transformant according to claim 7, wherein the host cell is an animal cell.

9. The transformant according to claim 8, wherein the host cell is a Chinese Hamster Ovary (CHO) cell.

10. A composition comprising the recombinant vector of claim 2 and a pharmaceutically acceptable carrier.

11. An in vitro method for preparing a target protein, comprising the steps of:

1) culturing the transformant of claim 7;
2) inducing the expression of a target protein from the transformant; and
3) harvesting the expressed target protein from the transformant or the culture solution thereof.

12. The method according to claim 11, wherein the target protein is selected from the group consisting of human growth hormones, growth hormone release hormones, growth hormone release peptides, interferons, interferon receptors, colony stimulating factors, glucagons-like peptides, G-protein-coupled receptors, interleukins, interleukin receptors, enzymes, interleukin- or cytokine-binding proteins, macrophage activating factors, macrophage peptides, B cell factors, T cell factors, protein A, allergy inhibitors, cell necrosis glycoprotein, immune toxins, lymph toxins, tumor necrosis factors, tumor suppressing factors, transitional growth factors, alpha-1 antitrypsin, albumin, alpha-lactalbumin, apolipoprotein-E, erythropoietin, highly glycosylated erythropoietin, angiopoietin, hemoglobin, thrombin, thrombin receptor activating peptides, thrombomodulin, blood factor VII, Vila, VIII, IX, and XIII, plasminogen activating factor, fibrin-binding peptides, urokinases, streptokinases, hirudin, protein C, C-reactive proteins, rennin inhibitors, collagenase inhibitors, superoxide dismutases, leptin, platelet-originated growth factor, epithelial growth factor, epidermal growth factor, angiostatin, angiotensin, myelopoiesis growth factor, myelopoiesis stimulating factor, calcitonin, insulin, atriopeptin, cartilage inducer, elcatonin, joint tissue activating factor, tissue factor pathway inhibitor, follicle stimulating hormone, progesterone forming hormone, progesterone forming hormone releasing hormone, nerve growth factors, parathormone, relaxin, cycretin, somatomedine, insulin-like growth factor, adrenocortical hormones, glucagons, cholecystokynine, pancreatic polypeptides, gastrin releasing peptide, corticotropin releasing factor, thyroid stimulating hormone, autotaxin, lactoferrin, myostatin, receptors, receptor antagonists, cell surface antigens, virus-originated vaccine antigens, monoclonal antibodies, polyclonal antibodies, and antibody fragments.

* * * * *